United States Patent
Lynch et al.

(10) Patent No.: US 6,642,051 B1
(45) Date of Patent: Nov. 4, 2003

(54) AMPLIFIABLE ADENO-ASSOCIATED VIRUS (AAV) PACKAGING CASSETTES FOR THE PRODUCTION OF RECOMBINANT AAV VECTORS

(75) Inventors: Carmel M. Lynch, Kenmore, WA (US); Haim Burstein, Redmond, WA (US); Anthony M. Stepan, Seattle, WA (US); Dara H. Lockert, Seattle, WA (US)

(73) Assignee: Targeted Genetics Corporation, Seattle, WA (US)

( * ) Notice: Subject to any disclaimer, the term of this patent is extended or adjusted under 35 U.S.C. 154(b) by 0 days.

(21) Appl. No.: 09/180,114

(22) PCT Filed: Oct. 20, 1998

(86) PCT No.: PCT/US98/21938

§ 371 (c)(1),
(2), (4) Date: Oct. 20, 1998

(87) PCT Pub. No.: WO99/20779

PCT Pub. Date: Apr. 29, 1999

Related U.S. Application Data

(60) Provisional application No. 60/090,109, filed on Oct. 21, 1997.

(51) Int. Cl.$^7$ ............................ C12N 5/10; C12N 15/63; C12N 15/64; C12N 15/864
(52) U.S. Cl. .................. 435/455; 435/320.1; 435/69.1; 435/325; 435/366; 435/369; 435/235.1; 435/91.4; 435/91.41; 435/91.42; 435/456; 435/457; 536/23.1; 536/23.72
(58) Field of Search .............................. 435/320.1, 69.1, 435/369, 325, 366, 235.1, 91.4, 91.41, 91.42, 455, 456, 457; 536/23.1, 23.72

(56) References Cited

U.S. PATENT DOCUMENTS

| | | | |
|---|---|---|---|
| 5,173,414 A | 12/1992 | Lebkowski et al. | |
| 5,354,678 A | 10/1994 | Lebkowski et al. | |
| 5,587,308 A | 12/1996 | Carter et al. | |
| 5,658,776 A | 8/1997 | Flotte et al. | |
| 5,837,484 A | 11/1998 | Trempe et al. | |
| 5,869,305 A | 2/1999 | Samulski et al. | |
| 5,990,279 A | 11/1999 | Carter et al. | |
| 6,338,962 B1 * | 1/2002 | Boyce | 435/320.1 |

FOREIGN PATENT DOCUMENTS

| | | |
|---|---|---|
| EP | 0 488 528 A1 | 6/1992 |
| WO | WO 92/08796 | 5/1992 |
| WO | WO 94/13788 | 6/1994 |
| WO | WO 94/28143 | 12/1994 |
| WO | WO 95/06743 | 3/1995 |
| WO | WO 95-13365 | 5/1995 |
| WO | WO 95/13365 * | 5/1995 |
| WO | WO 95/13392 | 5/1995 |
| WO | WO 95/14771 | 6/1995 |
| WO | WO 95/20671 | 8/1995 |
| WO | WO 96/00587 | 1/1996 |
| WO | WO 96/17947 | 6/1996 |
| WO | WO 97/09441 * | 3/1997 |
| WO | WO 97-09441 | 3/1997 |
| WO | WO 97/09442 | 3/1997 |
| WO | WO 97/32990 | 9/1997 |
| WO | WO 98/27204 | 6/1998 |

OTHER PUBLICATIONS

Samulski et al., J. Virol., vol. 63, No. 9, pp. 3822–3828, Sep. 1989.*
Samulski et al., J. Virol., 1989, vol. 63, No. 9, pp. 3822–3828.*
Urcelay et al., J. Virol., 1995, vol. 69, No. 4, pp. 2038–2046.*
Afione, S.A. et al., (May 1996) "In vivo model of adeno-associated virus vector persistence and rescue" *J. Virol.* 70(5):3235–3241.
Antoni, B.A. et al., (Jan. 1991) "Adeno–associated virus rep protein inhibits human immunodeficiency virus type 1 production in human cells" *Journal of Virology* 65(1):396–404.
Arispe, N. et al., (Mar. 1992) "Intrinsic anion channel activity of the recombinant first nucleotide binding fold domain of the cystic fibrosis transmembrane regulator protein" *Proc. Natl. Acad. Sci. USA*, Cell Biology, 89:1539–1543.
Ausubel, F.M. et al., eds. (1987) *Current Protocols in Molecular Biology*, John Wiley & Sons, Inc., Table of Contents: pp. iii–xii.
Berns, K.I. (1990) "Chapter 62: Parvoviridae and their replication" *Virology*, vol. 2, Fields, B.N. et al. (eds.), Raven Press (New York), pp. 1743–1763.
Blacklow, N.R. (1988) "Chapter 11 Adeno–associated viruses of humans" *Parvoviruses and Human Disease*, J.R. Pattison (ed.), CRC Press, Inc., pp. 165–174.
Boshart, M. et al., (Jun. 1985) "A very strong enhancer is located upstream of an immediate early gene of human cytomegalovirus" *Cell* 41:521–530.
Boulikas, T. (1996) "Common structural features of replication origins in all life forms" *J. Cell. Biochem.* 60:297–316.
Carter, B.J. (1989) "Chapter 18: Parvoviruses as vectors" *Handbook of Parvoviruses*, Vol. II, Tijssen, P. (ed.) CRC Press, Boca Raton, FL, pp. 247–284.

(List continued on next page.)

Primary Examiner—David Guzo
(74) Attorney, Agent, or Firm—Morrison & Foerster LLP

(57) ABSTRACT

High-efficiency AAV packaging constructs and methods for their use are provided. in the present invention. These high-efficiency packaging constructs comprise an activating element (such as the P1 sequence located within the AAV S1 integration site of human chromosome 19) amplifiably linked to one or more AAV packaging genes. The constructs may be either integrated into a mammalian cell genome or maintained episomally. Use of the high-efficiency AAV packaging vectors of the invention provides for controlled amplifiable production of rAAV vector constructs.

24 Claims, 5 Drawing Sheets

OTHER PUBLICATIONS

Carter, B.J. (1992) "Adeno–associated virus vectors" *Current Opinions in Biotechnology*, 3:533–539.

Carter, B.J. (1989) "Chapter 11: AAV DNA replication, integration, and genetics" *Handbook of Parvoviruses*, vol. I, Tijssen, P. (ed.) CRC Press, Boca Raton, FL, pp. 169–226.

Chatterjee, S. et al., (1991) "Transduction of intracellular resistance to HIV production by an adeno–associated virus–based antisense vector" *Vaccines 91*, Cold Spring Harbor Laboratory Press, Chanock, R.M. et al. (eds.), pp. 85–90.

Chatterjee, S. et al., (Nov. 27, 1992) "Dual–target inhibition of HIV–1 in vitro by means of an adeno–associated virus antisense vector" *Science* 258:1485–1488.

Chejanovsky, N. and Carter, B.J. (1989) "Mutagenesis of an AUG codon in the adeno–associate virus rep gene: Effects on viral DNA replication" *Virology* 173:120–128.

Clowes, M.M. et al., (Feb. 1994) "Long–term biological response of injured rat carotid artery seeded with smooth muscle cells expressing retrovirally introduced human genes" *J. Clin. Invest.* 93:644–651.

Coligan, J.E. et al., eds., (1998) in *Current Protocols in Immunology*, vol. 1, John Wiley & Sons, Inc., Table of Contents: pp. 1–9.

Colowick, P. (ed. in chief) et al., (1979) *Methods in Enzymology, vol. LVIII, Cell Culture*, Academic Press, Table of Contents: v–viii.

Diffley, J. (1996) "Once and only once upon a time: specifying and regulating origins of DNA replication in eukaryotic cells" *Genes & Devel.* 10:2819–2830.

Egan, M. et al., (Aug. 13, 1992) "Defective regulation of outwardly rectifying Cl channels by protein kinase A corrected by insertion of CFTR" *Nature* 358:581–584.

Fareed, G.C. et al., (1980) "Electron microscopic methods for locating the origin and termination points for DNA replication" *Methods in Enzymology*, vol. 65, Grossman, L. and Moldave, K. eds., Academic Press, New York, pp. 709–717.

Flotte, T.R. et al., (1992) "Gene expression from adeno–associated virus vectors in airway epithelial cells" *Am. J. Respir. Cell. Mol. Biol.* 7:349–356.

Flotte, T.R. et al., (1993) "Expression of the cystic fibrosis transmembrane conductance regulator from a novel adeno–associated virus promoter" *J. Biol. Chem.* 268(5):3781–3790.

Flotte, T.R. et al., (Nov. 1993) "Stable in vivo expression of the cystic fibrosis transmembrane conductance regulator with an adeno–associate virus vector" *Proc. Natl. Acad. Sci. USA*. Medical Sciences 93:10613–10617.

Flotte et al., (1995) "An improved system for packaging recombinant adeno–associated virus vectors capable of in vivo transduction" *Gene Ther.* 2:29–37.

Freshney, R.I. ed. (1987) in *Animal cell culture: a practical approach*, IRL Press, Oxford, Table of Contents: pp. vii–xii.

Gait, M.J. ed. (1984) *Oligonucleotide synthesis. a practical approach*, IRL Press, Oxford, Table of Contents: pp. vii–xii.

Hermonat, P.L. and Muzyczka, N. (Oct. 1984) "Use of adeno–associated virus as a mammalian DNA cloning vector: Transduction of neomycin resistance into mammalian tissue culture cells" *Proc. Natl. Acad. Sci. USA* Genetics 81:6466–6470.

Hermonat, P.L. et al., (Aug. 1984) "Genetics of adeno–associated virus: Isolation and preliminary characterization of adeno–associated virus type 2 mutants" *J. Virol.* 51(2):329–339.

Hölscher, C. et al., (1994) "Cell lines inducibly expressing the adeno–associated virus (AAV) rep gene: Requirements for productive replication of rep–negative AAV mutants" *J. Virol.* 68(11):7169–7177.

Hölscher, C. et al., (Nov. 1995) "High–level expression of adeno–associated virus (AAV) rep78 or rep68 protein is sufficient for infectious–particle formation by a rep–negative AAV mutant" *J. Virol.* 69(11):6880–6885.

Kaplitt, M.G. et al., (Oct. 1994) "Long–term gene expression and phenotypic correction using adeno–associated virus in the mammalian brain" *Nature Genetics* 8:148–154.

Kelman, Z. and O'Donnell, M. (1994) "DNA replication: Enzymology and mechanisms" *Curr. Opin. Genet. Dev.* 4:185–195.

Khleif, S.N. et al., (1991) "Inhibition of cellular transformation by the adeno–associated virus rep gene" *Virology* 181:738–741.

Kornberg, A. and Baker, T.A. (1992) *DNA Replication*, Second Edition, Freeman, W.H. & Co., New York, Table of Contents: v–ix.

Kotin, R.M. et al., (Dec. 1992) "Characterization of a preferred site on human chromosone 19q for integration of adeno–associated virus DNA by non–homologous recombination" *The EMBO J.* 11(13):5071–5078.

Labow, M.A. et al., (Apr. 1987) "Adeno–associated virus gene expression inhibits cellular transformation by heterologous genes" *Mol. Cell. Biol.* 7(4):1320–1325.

Laface, D. et al. (Feb. 1988) "Gene transfer into hematopoietic progenitor cells mediated by an adeno–associated virus vector" *Virology* 162(2):483–486.

Laughlin, C.A. et al., (Nov. 1979) "Spliced adenovirus–associated virus RNA" *Proc. Natl. Acad. Sci. USA* Biochemistry 76(11):5567–5571.

Laughlin, C.A. et al., (1983) "Cloning of infectious adeno–associated virus genomes in bacterial plasmids" *Gene* 23:65–73.

Lebkowski, J.S. et al., (Oct. 1988) "Adeno–associated virus: A vector system for efficient introduction and integration of DNA into a variety of mammalian cell types" *Mol. Cell. Biol.* 8(10):3988–3996.

Lupton, S.D. et al., (Jun. 1991) "Dominant positive and negative selection using a hygromycin phosphotransferase–thymidine kinase fusion gene" *Molecular and Cellular Biology* 11(6):3374–3378.

Lynch, C.M. et al., (Apr. 1997) "Adeno–associated virus vectors for vascular gene delivery" *Circ. Res.* 80(4):497–505.

McLaughlin, S.K. et al., (Jun. 1988) "Adeno–associated virus general transduction vectors: Analysis of proviral structures" *J. Virol.* 62(6):1963–1973.

Mendelson, E. et al., (1988) "Expression and rescue of a nonselected marker from an integrated AAV vector" *Virology* 166:154–165.

Miller, J.H. and Calos, M.P. eds., (1987) *Current Communications in Molecular Biology, Gene transfer vectors for mammalian cells*, Cold Spring Harbor Laboratory, Table of Contents: vii–ix.

Muro–Cacho, C.A. et al., (1992) "Gene Transfer in human lymphocytes using a vector based on adeno–associated virus" *J. Immunotherapy* 11(4):231–237.

Muzyczka, N. (1992) "Use of adeno–associated virus as a general transduction vector for mammalian cells" *Current Topics in Microbiol. and Immunol.* 158:97–129.

Rich, D.P. et al., (Jul. 12, 1991) "Effect of deleting the R domain on CFTR–generated chloride channels" *Science* 253:205.207.

Rose, J.A. (1974) "Chapter 1: Parvovirus reproduction" *Comprehensive Virology* 3:1–61.

Sambrook, J. et al., (1989) *Molecular cloning: a laboratory manual*, 2nd edition, Cold Spring Harbor Laboratory Press, Table of Contents: xi–xxxviii.

Samulki, R.J. et al., (Sep. 1989) "Helper–free stocks of recombinant adeno–associated viruses: Normal integration does not require viral gene expression" *J. Virol.* 63(9):3822–3828.

Samulski, R.J. et al., (Mar. 1982) "Cloning of adeno–associated virus into pBR322: Rescue of intact virus from the recombinant plasmid in human cells" *Proc. Natl. Sci. USA* Microbiology 79:2077–2081.

Samulski, R.J. et al., (Oct. 1987) "A recombinant plasmid from which an infectious adeno–associated virus genome can be excised in vitro and its use to study viral replication" *J. Virol.* 61(10):3096–3101.

Senapathy, P. and Carter, B.J. (Apr. 10, 1984) "Molecular cloning of adeno–associated virus variant genomes and generation of infectious virus by recombination in mammalian cells" *J. Biol. Chem.* 259(7):4661–4666.

Sheppard, D.N. et al., (Mar. 25, 1994) "The amino–terminal portion of CFTR forms a regulated Cl channel" *Cell* 76:7091–1098.

Simonsen, C.C. et al., (May 1983) "Isolation and expression of an altered mouse dihydrofolate reductase cDNA" *Proc. Natl. Acad. Sci. USA* Biochemistry 80:2495–2499.

Srivastava, A. et al., (Feb. 1983) "Nucleotide sequence and organization of the adeno–associated virus 2 genome" *J. Virol.* 45(2):555–564.

Srivastiva, C.H. et al., (Oct. 1989) "Construction of a recombinant human parvovirus B 19: Adeno–associated virus 2 (AAV) DNA inverted terminal repeats are functional in an AAV–B 19 hybrid virus" *Proc. Natl. Acad. Sci. USA*, Medical Sciences 86:8078–8082.

Tratschin, J.–D. et al., (Sep. 1984) "Genetic analysis of adeno–associated virus: Properties of deletion mutants constructed in vitro and evidence for an adeno–associated virus replication function" *J. Virol.* 51(3):611–619.

Tratschin, J.–D. et al., (Oct. 1984) "A human parvovirus, adeno–associated virus, as a eucaryotic vector: Transient expression and encapsidation of the procaryotic gene for chloramphenicol acetyltransferase" *Mol. Cell. Biol.* 4(10):2072–2081.

Tratschin, J.–D. et al., (Nov. 1985) "Adeno–associated virus vector for high–frequency integration, expression, and rescue of genes in mammalian cells" *Moll. Cell. Biol.* 5(11):3251–3260.

Tratschin, J.–D. et al., (Aug. 1986) "Negative and positive regulation in trans of gene expression from adeno–associated virus vectors in mammalian cells by a viral rep gene product" *Mol. Cell. Biol.* 6(8):2884–2894.

Vincent, K.A. et al., (1990) "Replication and packaging of HIV envelope genes in a novel adeno–associated virus vector system" *Vaccine 90*, Cold Spring Harbor Laboratory Press, Brown, F. et al. (eds.) pp. 353–359.

Walsh, C.E. et al., (Aug. 1992) "Regulated high level expression of a human γ–globin gene introduced into erythroid cells by an adeno–associated virus vector" *Proc. Natl. Acad. Sci. USA* Medical Sciences 89:7257–7261.

Weir, D.M. ed. et al., (1996) "*Immunochemistry and molecular immunology*" in Weir's *Handbook of Experimental Immunology*, Fifth Edition, vol. 1, Table of Contents: v–xii.

Weitzman, M. D. et al., (Jun. 1994) "Adeno–associated virus (AAV) rep proteins mediate complex formation between AAV DNA and its integration site in human DNA" *Proc. Natl. Acad. Sci. USA* Biochemistry 91:5808–5817.

Wong, K.K. et al., (1991) "Restriction of HSV–1 production in cell lines transduced with an antisense viral vector targeting the ICP4 gene" *Vaccine 91*, Cold Spring Harbor Laboratory Press, pp. 183–189.

Xiao, X. (Feb. 1997). "A Novel 165–Base–Pair Terminal Repeat Sequence Is the Sole cis Requirement for the Adeno–Associated Virus Life Cycle," *Journal of Virology* 71(2):941–948.

Giraud, C. et al., (Nov. 1995) "Recombinant junctions formed by site–specific integration of adeno–associated virus into an episome" *J. Virol.* 69(11):6917–6924.

Giraud, C. et al., (Oct. 1994) "Site–specific integration by adeno–associated virus is directed by a cellular DNA sequence" *Proc. Natl. Acad. Sci. USA*, Microbiology 91:10039–10043.

Linden, R.M. et al., (Oct. 1996) "Site–specific integration by adeno–associated virus" *Proc. Natl. Acad. Sci. USA* Colloquium Paper 93:11288–11294.

Urcelay, E. et al., (Apr. 1995) "Asymmetric replication in vitro from a human sequence element is dependent on adeno–associated virus rep protein" *J. Virol.* 69(4):2038–2046.

* cited by examiner

AMPLIFIABLE ADENO-ASSOCIATED VIRUS (AAV) PACKAGING CASSETTES FOR THE PRODUCTION OF RECOMBINANT AAV VECTORS

This application claims benefit of the provisional application No. 60/090,109, filed Oct. 21,1997.

TECHNICAL FIELD

This invention is in the field of viral constructs for gene delivery. More specifically, the invention is in the field of recombinant DNA constructs for use in the production of adeno-associated virus (AAV) vectors for gene delivery.

BACKGROUND

Vectors based on adeno-associated virus (AAV) are believed to have utility for gene therapy but a significant obstacle has been the difficulty in generating such vectors in amounts that would be clinically useful for human gene therapy applications. This is a particular problem for in vivo applications such as direct delivery to the lung. Another important goal in the gene therapy context, discussed in more detail herein, is the production of vector preparations that are essentially free of replication-competent virions. The following description briefly summarizes studies involving adeno-associated virus and AAV vectors, and then describes a number of novel improvements according to the present invention that are useful for efficiently generating high titer recombinant AAV vector (rAAV) preparations suitable for use in gene therapy.

Adeno-associated virus is a defective parvovirus that grows only in cells in which certain functions are provided by a co-infecting helper virus. General reviews of AAV may be found in, for example, Carter, 1989, *Handbook of Parvoviruses*, Vol. I, pp. 169–228, and Berns, 1990, *Virology*, pp. 1743–1764, Raven Press, (New York). Examples of co-infecting viruses that provide helper functions for AAV growth and replication are adenoviruses, herpesviruses and, in some cases, poxviruses such as vaccinia. The nature of the helper function is not entirely known but it appears that the helper virus indirectly renders the cell permissive for AAV replication. This belief is supported by the observation that AAV replication may occur at low efficiency in the absence of helper virus co-infection if the cells are treated with agents that are either genotoxic or that disrupt the cell cycle.

Although AAV may replicate to a limited extent in the absence of helper virus, under such conditions as noted above, more generally infection of cells with AAV in the absence of helper functions results in the proviral AAV genome integrating into the host cell genome. Unlike other viruses, such as many retroviruses, it appears that AAV generally integrates into a unique position in the human genome. Thus, it has been reported that, in human cells, AAV integrates into a unique position (referred to as an "AAV integration site") which is located on chromosome 19. See, e.g., Weitzman et al. (1994) *Proc. Nat'l. Acad. Sci. USA* 91: 5808–5812. If host cells having an integrated AAV are subsequently superinfected with a helper virus such as adenovirus, the integrated AAV genome can be rescued and replicated to yield a burst of infectious progeny AAV particles. A sequence at the AAV integration site, referred to as "P1," shares homology with the AAV inverted terminal repeat (ITR) sequence, exhibits activity in a cell-free replication system, and is believed to be involved in both the integration and rescue of AAV. See, e.g., Weitzman et al., id., Kotin et al. (1992) *EMBO J.* 11:5071–5078, and Urcelay et al., *J. Virol.* 69: 2038–2046. The fact that integration of AAV appears to be efficient and site-specific makes AAV a useful vector for introducing genes into cells for uses such as human gene therapy.

AAV has a very broad host range without any obvious species or tissue specificity and can replicate in virtually any cell line of human, simian or rodent origin provided that an appropriate helper is present. AAV is also relatively ubiquitous and has been isolated from a wide variety of animal species including most mammalian and several avian species.

AAV is not associated with the cause of any disease. Nor is AAV a transforming or oncogenic virus, and integration of AAV into the genetic material of human cells generally does not cause significant alteration of the growth properties or morphological characteristics of the host cells. These properties of AAV also recommend it as a potentially useful human gene therapy vector because most of the other viral systems proposed for this application, such as retroviruses, adenoviruses, herpesviruses, or poxviruses, are disease-causing.

Although various serotypes of AAV are known to exist, they are all closely related functionally, structurally, and at the genetic level (see, e.g., Blacklow, 1988, pp. 165–174 of *Parvoviruses and Human Disease*, J. R. Pattison (ed.); and Rose, 1974, *Comprehensive Virology* 3: 1–61). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to inverted terminal repeats (ITRs). The similar infectivity patterns also suggest that the replication functions in each serotype are under similar regulatory control. Thus, although the AAV2 serotype was used in various illustrations of the present invention that are set forth in the Examples, general reference to AAV herein encompasses all AAV serotypes, and it is fully expected that the methods and compositions disclosed herein will be applicable to all AAV serotypes.

AAV particles are comprised of a proteinaceous capsid having three capsid proteins, VP1, VP2 and VP3, which enclose a DNA genome. The AAV2 DNA genome, for example, is a linear single-stranded DNA molecule having a molecular weight of about $1.5 \times 10^6$ daltons and a length of about 5 kb. Individual particles package only one DNA molecule strand, but this may be either the "plus" or "minus" strand. Particles containing either strand are infectious and replication occurs by conversion of the parental infecting single strand to a duplex form and subsequent amplification of a large pool of duplex molecules from which progeny single strands are displaced and packaged into capsids. Duplex or single-strand copies of AAV genomes can be inserted into bacterial plasmids or phagemids and transfected into adenovirus-infected cells; these techniques have facilitated the study of AAV genetics and the development of AAV vectors.

The AAV genome, which encodes proteins mediating replication and encapsidation of the viral DNA, is generally flanked by two copies of inverted terminal repeats (ITRs). In the case of AAV2, for example, the ITRs are each 145 nucleotides in length, flanking a unique sequence region of about 4470 nucleotides that contains two main open reading frames for the rep and cap genes (Srivastiva et al., 1983, *J. Virol.*, 45:555–564; Hermonat et al., *J. Virol.* 51:329–339; Tratschin et al., 1984a, *J. Virol.*, 51:611–619). The AAV2 unique region contains three transcription promoters p5, p19, and p40 (Laughlin et al., 1979, *Proc. Natl. Acad. Sci. USA*, 76:5567–5571) that are used to express the rep and cap genes. The ITR sequences are required in cis and are sufficient to provide a functional origin of replication (ori), signals required for integration into the cell genome, and efficient excision and rescue from host cell chromosomes or recombinant plasmids. It has also been shown that the ITR can function directly as a transcription promoter in an AAV vector. See Flotte et al., 1993, supra; and Carter et al., U.S. Pat. No. 5,587,308.

The rep and cap gene products are required in trans to provide functions for replication and encapsidation of viral genome, respectively. Again, using AAV2 for purposes of illustration, the rep gene is expressed from two promoters, p5 and p19, and produces four proteins. Transcription from p5 yields an unspliced 4.2 kb mRNA encoding a first Rep protein (Rep78), and a spliced 3.9 kb mRNA encoding a second Rep protein (Rep68). Transcription from p19 yields an unspliced mRNA encoding a third Rep protein (Rep52), and a spliced 3.3 kb mRNA encoding a fourth Rep protein (Rep40). Thus, the four Rep proteins all comprise a common internal region sequence but differ in their amino and carboxyl terminal regions. Only the large Rep proteins (i.e. Rep78 and Rep68) are required for AAV duplex DNA replication, but the small Rep proteins (i.e. Rep52 and Rep40) appear to be needed for progeny, single-strand DNA accumulation (Chejanovsky & Carter, 1989, *Virology* 173:120–128). Rep68 and Rep78 bind specifically to the hairpin conformation of the AAV ITR and possess several enzyme activities required for resolving replication at the AAV termini. Rep52 and Rep40 have none of these properties. Reports by C. Hölscher et al. (1994, *J. Virol.* 68:7169–7177; and 1995, *J. Virol.* 69:6880–6885) have suggested that expression of Rep78 or Rep 68 may in some circumstances be sufficient for infectious particle formation.

The Rep proteins, primarily Rep78 and Rep68, also exhibit pleiotropic regulatory activities including positive and negative regulation of AAV genes and expression from some heterologous promoters, as well as inhibitory effects on cell growth (Tratschin et al., 1986, *Mol. Cell. Biol.* 6:2884–2894; Labow et al., 1987, *Mol. Cell. Biol.*, 7:1320–1325; Khleif et al., 1991, *Virology*, 181:738–741). The AAV p5 promoter is negatively auto-regulated by Rep78 or Rep68 (Tratschin et al., 1986, *Mol. Cell. Biol.* 6:2884–2894). Due to the inhibitory effects of expression of rep on cell growth, constitutive expression of rep in cell lines has not been readily achieved. For example, Mendelson et al. (1988, *Virology*, 166:154–165) reported very low expression of some Rep proteins in certain cell lines after stable integration of AAV genomes.

The capsid proteins VP1, VP2, and VP3 share a common overlapping sequence, but VP1 and VP2 contain additional amino terminal sequences. All three proteins are encoded by the same cap gene reading frame typically expressed from a spliced 2.3 kb mRNA transcribed from the p40 promoter. VP2 and VP3 can be generated from this mRNA by use of alternate initiation codons. Generally, transcription from p40 yields a 2.6 kb precursor mRNA which can be spliced at alternative sites to yield two different transcripts of about 2.3 kb. VP2 and VP3 can be encoded by either transcript (using either of the two initiation sites), whereas VP1 is encoded by only one of the transcripts. VP3 is the major capsid protein, typically accounting for about 90% of total virion protein. VP1 is coded from a minor mRNA using a 3' donor site that is 30 nucleotides upstream from the 3' donor used for the major mRNA that encodes VP2 and VP3. All three proteins are required for effective capsid production. Mutations which eliminate all three proteins (Cap-negative) prevent accumulation of single strand progeny AAV DNA, whereas mutations in the VP1 amino-terminus ("Lip-negative" or "Inf-negative") can permit assembly of single-stranded DNA into particles but the infectious titer is greatly reduced.

The genetic analysis of AAV that was highlighted above was largely based upon mutational analysis of AAV genomes cloned into bacterial plasmids. In early work, molecular clones of infectious genomes of AAV were constructed by insertion of double-strand molecules of AAV into plasmids by procedures such as GC-tailing (Saimulski et al., 1982, *Proc. Natl. Acad. Sci. USA*, 79:2077–2081), addition of synthetic linkers containing restriction endonuclease cleavage sites (Laughlin et al., 1983, *Gene*, 23:65–73) or by direct, blunt-end ligation (Senapathy & Carter, 1984, *J. Biol. Chem.*, 259:46614666). Transfection of such AAV recombinant plasmids into mammalian cells that were also infected with an appropriate helper virus, such as adenovirus, resulted in rescue and excision of the AAV genome free of any plasmid sequence, replication of the rescued genome and generation of progeny infectious AAV particles. This provided the basis for performing genetic analysis of AAV as summarized above and permitted construction of AAV transducing vectors.

Based on the genetic analysis, the general principles of AAV vector construction were defined as reviewed recently (Carter, 1992, *Current Opinions in Biotechnology*, 3:533–539; Muzyczka, 1992, *Curr. Topics in Microbiol. and Immunol.*, 158:97–129). AAV vectors are generally constructed in AAV recombinant plasmids by substituting portions of the AAV coding sequence with foreign DNA to generate a recombinant AAV (rAAV) vector or "pro-vector". In the vector, the terminal (ITR) portions of the AAV sequence must generally be retained intact because these regions are generally required in cis for several functions, including excision from the plasmid after transfection, replication of the vector genome and integration and rescue from a host cell genome. In some situations, providing a single ITR may be sufficient to carry out the functions normally associated with two wild-type ITRs (see, e.g., Samulski et al., WO 94/13788, published Jun. 23, 1994).

The vector can then be packaged into an AAV particle to generate an AAV transducing virus by transfection of the vector into cells that are infected by an appropriate helper virus such as adenovirus or herpesvirus; provided that, in order to achieve replication and encapsidation of the vector genome into AAV particles, the vector must generally be complemented for any AAV functions required in trans, particularly rep and cap, that were deleted in construction of the vector.

Such AAV vectors are among a small number of recombinant virus vector systems which have been shown to have utility as in vivo gene transfer agents (reviewed in Carter, 1992, *Current Opinion in Biotechnology*, 3:533–539; Muzyczka, 1992, *Curr. Top. Microbiol Immunol.* 158:97–129) and thus are potentially of great importance for human gene therapy. AAV vectors are capable of high-frequency transduction and expression in a variety of cells including cystic fibrosis (CF) bronchial and nasal epithelial cells (see, e.g., Flotte et al., 1992a, *Am. J. Respir. Cell Mol. Biol.* 7:349–356; Egan et al., 1992, *Nature*, 358:581–584; Flotte et al., 1993a, *J. Biol. Chem.* 268:3781–3790; and Flotte et al., 1993b, *Proc. Natl. Acad. Sci. USA*, 93:10163–10167); human bone marrow-derived erythroleukemia cells (see, e.g., Walsh et al., 1992, *Proc. Natl. Acad. Sci. USA*, 89:7257–7261); as well as brain, eye and muscle cells. AAV may not require active cell division for transduction and expression which would be another clear advantage over retroviruses, especially in tissues such as the human airway epithelium where most cells are terminally differentiated and non-dividing.

There are at least two desirable features of any AAV vector designed for use in human gene therapy. The first is that the transducing vector be generated at titers sufficiently high to be practicable as a delivery system. This is especially important for gene therapy stratagems aimed at in vivo delivery of the vector. For example, it is likely that for many desirable applications of AAV vectors, such as treatment of cystic fibrosis by direct in vivo delivery to the airway, the desired dose of transducing vector may be from $10^8$ to $10^{10}$, or, in some cases, in excess of $10^{10}$ particles. Secondly, the vector preparations are preferably essentially free of wild-type AAV virus (or any replication-competent AAV). The attainment of high titers of AAV vectors has been difficult for several reasons including preferential encapsidation of wild-type AAV genomes (if they are present or generated by recombination), and the difficulty in generating sufficient complementing functions such as those provided by the wild-type rep and cap genes. Useful cell lines expressing such complementing functions have been especially difficult to generate, in part because of pleiotropic inhibitory functions associated with the rep gene products. Thus, cell lines in which the rep gene is integrated and expressed may grow slowly or express rep at very low levels.

The first AAV vectors described contained foreign reporter genes such as neo, cat or dhfr expressed from AAV transcription promoters or an SV40 promoter (Tratschin et al., 1984b, *Mol. Cell. Biol.* 4:2072–2081; Hermonat & Muzyczka, 1984, *Proc. Natl. Acad. Sci. USA*, 81:6466–6470; Tratschin et al., 1985, *Mol. Cell. Biol.* 5:3251–3260; McLaughlin et al., 1988, *J. Virol.*, 62:1963–1973; Lebkowski et al., 1988 *Mol. Cell. Biol.*, 7:349–356). These vectors were packaged into AAV-transducing particles by co-transfection into adenovirus-infected cells together with a second "packaging plasmid" containing the AAV rep and cap genes expressed from the wild-type AAV tanscription promoters. Several strategies have been employed in attempts to prevent encapsidation of the packaging plasmid. In some cases, (Hermonat & Muzyczka, 1984; McLaughlin et al., 1988) a large region of bacteriophage lambda DNA was inserted into the packaging plasmid within the AAV sequence to generate an oversized genome that could not be packaged. In other cases, (Tratschin et al., 1984b; Tratschin et al., 1985, Lebkowski et al., 1988), the packaging plasmid had deleted the ITR regions of AAV so that it could not be excised and replicated and thus could not be packaged. All of these approaches failed to prevent generation of particles containing replication-competent AAV DNA and also failed to generate effective high titers of AAV transducing particles. Indeed, titers of not more than $10^4$ infectious particles per ml were cited by Hermonat & Muzyczka, 1984.

In many studies, the presence of overlapping homology between AAV sequences present in the vector and packaging plasmids resulted in the production of replication-competent AAV particles. It was shown by Senapathy and Carter (1984, *J. Biol. Chem.* 259:4661–4666) that the degree of recombination in such a system is approximately equivalent to the degree of sequence overlap. It was suggested in a review of the early work (Carter 1989, *Handbook of Parvoviruses*, Vol. II, pp. 247–284, CRC Press, Boca Raton, Fla.) that titers of $10^6$ infectious particles per ml might be obtained, but this was based on the above-cited studies in which large amounts of replication-competent AAV contaminated the vector preparation. Such vector preparations containing replication-competent AAV will generally not be preferred for human gene therapy. Furthermore, these early vectors exhibited low transduction efficiencies and did not transduce more than 1 or 2% of cells in cultures of various human cell lines even though the vectors were supplied at multiplicities of up to 50,000 particles per cell. This may have reflected in part the contamination with replication-competent AAV particles and the presence of the AAV rep gene in the vector. Furthermore, Samulski et al. (1989, *J. Virol.* 63:3822–3828) showed that the presence of wild-type AAV significantly enhanced the yield of packaged vector. Thus, in packaging systems where the production of wild-type AAV is eliminated, the yield of packaged vector may actually be decreased. Nevertheless, for use in any human clinical application it will be preferable to essentially eliminate production of replication-competent AAV.

Additional studies (McLaughlin et al., 1988; Lebkowski et al., 1988) attempting to generate AAV vectors lacking the AAV rep or cap genes still generated replication-competent AAV and still produced very low transduction frequencies on human cell lines. Thus, McLaughlin et al., 1988 reported that AAV rep-negative cap-negative vectors containing the neo gene packaged with the same packaging plasmid used earlier by Hermonat & Muzyczka (1984) still contained replication-competent AAV. As a consequence, it was only possible to use this virus at a multiplicity of 0.03 particles per cell (i.e., 300 infectious units per 10,000 cell) to avoid double hits with vector and wild-type particles. Thus, when 32,000 cells were infected with 1000 infectious units, an average of 800 geneticin-resistant colonies was obtained. Although this was interpreted as demonstrating that the virus was capable of yielding a transduction frequency of 80%, in fact only 2.5% of the cells were transduced. Thus the effectively useful titer of this vector was limited. Furthermore, this study did not demonstrate that the actual titer of the vector preparation was any higher than those obtained previously by Hermonat & Muzyczka (1984). Similarly, Lebkowski et al., 1988, packaged AAV vectors which did not contain either a rep or cap gene, using an ori-negative packaging plasmid (pBa1A) identical to that used earlier by Tratschin et al., (1984b, 1985), and reported transduction frequencies that were similarly low, in that for several human cell lines not more than 1% of the cells could be transduced to geneticin resistance even with their most concentrated vector stocks. Lebkowski et al., (1988) did not report the actual vector titers in a meaningful way but the biological assays, showing not more than 1% transduction frequency when $5 \times 10^6$ cells were exposed to three ml of vector preparation, indicate that the titer was less than $2 \times 10^4$ geneticin resistant units per ml. Also, the pBa1A packaging plasmid contains overlapping homology with the ITR sequence in the vector and can lead to generation of replication-competent AAV by homologous recombination.

Laface et al. (1988) used the same vector as that used by Hermonat & Muzyczka (1984) prepared in the same way and obtained a transduction frequency of 1.5% in murine bone marrow cultures, again showing very low titer.

Samulski et al. (1987, *J. Virol.*, 61:3096–3101) constructed a plasmid called pSub201 which contained an intact AAV genome in a bacterial plasmid but which had a deletion of 13 nucleotides at the extremity of each ITR and thus was rescued and replicated less efficiently than other AAV plasmids that contained the entire AAV genome. Samulski et al. (1989, *J. Virol.*, 63:3822–3828) constructed AAV vectors based on pSub201 but deleted for rep and cap and containing either a hyg or neo gene expressed from an SV40 early gene promoter. They packaged these vectors by co-transfection with a packaging plasmid called pAAV/Ad which consisted of the entire AAV nucleotide sequence from nucleotide 190 to 4490 enclosed at either end with one copy of the adenovirus ITR. In this packaging plasmid the AAV rep and cap genes were expressed from their native AAV promoters (i.e. p5, p19 and p40, as discussed above). The function of the adenovirus ITR in pAAV/Ad was thought to enhance the expression level of AAV capsid proteins. However, rep is expressed from its homologous promoter and is negatively regulated and thus its expression is limited. Using their encapsidation system, Samulski et al. generated AAV vector stocks that were substantially free of replication-competent AAV but had transducing titers of only $3\times10^4$ hygromycin-resistant units per ml of supernatant. When a wild-type AAV genome was used in the packaging plasmid, the titer of the AAV vector prep was increased to $5\times10^4$ hygromycin-resistant units per ml. The low titer produced in this system thus appears to have been due in part to the defect in the ITR sequences of the basic pSub201 plasmid used for vector construction and in part due to limiting expression of AAV genes from pAAV/Ad. In an attempt to increase the titer of the AAVneo vector preparation, Samulski et al. generated vector stocks by transfecting, in bulk, thirty 10-cm dishes of 293 cells and concentrating the vector stock by banding in CsCl. This produced an AAVneo vector stock containing a total of $10^8$ particles as measured by a DNA dot-blot hybridization assay. When this vector stock was used at multiplicities of up to 1,000 particles per cell, a transduction frequency of 70% was obtained. This suggests that the particle-to-transducing ratio is about 500 to 1,000 particles since at the ratio of one transducing unit per cell the expected proportion of cells that should be transduced is 63% according to the Poisson distribution.

Although the system of Samulski et al. (1989), using the vector plasmid pSub201 and the packaging plasmid pAAV/Ad, did not have overlapping AAV sequence homology between the two plasmids, there is overlapping homology at the XbaI sites and recombination of these sites can lead to the generation of complete replication-competent AAV. That is, although overlapping homology of AAV sequence is not present, the complete AAV sequence is contained within the two plasmids and the plasmids share a short (non-AAV) sequence that might facilitate recombination to generate replication-competent AAV, which is undesirable. That this class of recombination occurs in AAV plasmids was shown by Senapathy & Carter (1984, *J. Biol. Chem.* 259:466–4666). Given the problems of low titer, and the capability of generating wild-type recombinants, the system described by Samulski et al., 1989, does not have practical utility for human gene therapy.

Several other reports have described AAV vectors. For example, Srivastiva et al., (1989, *Proc. Natl. Acad. Sci. USA*, 86:8078–8082) described an AAV vector based on the pSub201 plasmid of Samulski et al. (1987), in which the coding sequences of AAV were replaced with the coding sequences of another parvovirus, B19. This vector was packaged into AAV particles using the pAAV/Ad packaging plasmid to generate a functional vector, but titers were not reported. This system was based on pSub201 and thus suffers from the defect described above for this plasmid. Second, the vector and the packaging plasmid contained overlapping AAV sequences (the ITR regions) and thus recombination yielding contaminating wild-type virus is highly likely.

Chatterjee et al. (1991, *Vaccines* 91, Cold Spring Harbor Laboratory Press, pp. 85–89), Wong et al. (1991, *Vaccines* 91, Cold Spring Harbor Laboratory Press, pp. 183–189), and Chatterjee et al. (1992, *Science*, 258:1485–1488) describe AAV vectors designed to express antisense RNA directed against infectious viruses such as HIV or Herpes simplex virus. However, these authors did not report any titers of their AAV vector stocks. Furthermore, they packaged their vectors using an ori-negative packaging plasmid analogous to that used by Tratschin et al. (1984b, 1985) containing the Ba1A fragment of the AAV genome and therefore their packaging plasmid contained AAV vector sequences that have homology with AAV sequences that were present in their vector constructs. This will also lead to generation of replication-competent AAV. Thus, Chatteijee et al., and Wong et al., used a packaging system known to give only low titer and which can lead to generation of replication-competent AAV genomes because of the overlapping homology in the vector and packaging sequences.

Other reports have described the use of AAV vectors to express genes in human lymphocytes (Muro-Cacho et al., 1992, *J. Immunotherapy*, 11:231–237) or a human erythroid leukemia cell line (Walsh et al., 1992, *Proc. Natl. Acad. Sci. USA*, 89:7257–7261) with vectors based on the pSub201 vector plasmid and pAAV/Ad packaging plasmid. Again, titers of vector stocks were not reported and were apparently low because a selective marker gene was used to identify those cells that had been successfully transduced with the vector.

Transduction of human airway epithelial cells, grown in vitro from a cystic fibrosis patient, with an AAV vector expressing the selective marker gene neo from the AAV p5 promoter was reported (Flotte et al., 1992, *Am. J. Respir. Cell. Mol. Biol.* 7:349–356). In this study the AAVneo vector was packaged into AAV particles using the pAAV/Ad packaging plasmid. Up to 70% of the cells in the culture could be transduced to geneticin resistance and the particle-to-transducing ratio was similar to that reported by Samulski et al. (1989). Thus to obtain transduction of 70% of the cells, a multiplicity of up to several hundred vector particles per cell was required. Transduction of human airway epithelial cells in in vitro culture using an AAV transducing vector that expressed the cystic fibrosis transmembrane conductance regulator (CFTR) gene from the AAV ITR promoter showed that the cells could be functionally corrected for the electrophysiological defect in chloride channel function that exists in cells from cystic fibrosis patients (Egan et al., *Nature*, 1992, 358:581–584; Flotte et al., *J. Biol. Chem.* 268:3781–3790).

The above-cited studies suggest that AAV vectors have potential utility as vectors for treatment of human disease by gene therapy. However, the difficulty in generating sufficient amounts of AAV vectors has been a severe limitation on the development of human gene therapy using AAV vectors. One aspect of this limitation is that there have been very few studies using AAV vectors in in vivo animal models (see, e.g., Flotte et al., 1993b; and Kaplitt et al., 1994, *Nature Genetics* 8:148–154). This is generally a reflection of the difficulty associated with generating sufficient amounts of AAV vector stocks having a high enough titer to be useful in analyzing in vivo delivery and gene expression.

One of the limiting factors for AAV gene therapy has been the relative inefficiency of the vector packaging systems that have been used. In the absence of suitable cell lines expressing sufficient levels of the AAV trans complementing functions, such as rep and cap, packaging of AAV vectors has been achieved in adenovirus-infected cells by co-transfection of a packaging plasmid and a vector. The efficiency of this process is expected to be limited by the efficiency of transfection of each of the plasmid constructs, and by the low level of expression of Rep proteins from the packaging plasmids described to date. Each of these problems appears to relate to the biological activities of the AAV Rep proteins which are known to be associated with pleiotropic inhibitory effects. In addition, as noted above, all of the packaging systems described above have the ability to generate replication-competent AAV by recombination.

The difficulty in generating cell lines stably expressing functional Rep apparently reflects a cytotoxic or cytostatic. function of Rep as shown by the inhibition, by Rep protein, of neo-resistant colony formation (Labow et al., 1987; Trempe et al., 1991). This also appears to relate to the tendency of Rep to reverse the immortalized phenotype in cultured cells, which has made the production of cell lines stably expressing functional rep extremely difficult. Several attempts to generate cell lines expressing rep have been made. Mendelson et al., (1988, Virology, 166:154–165) reported obtaining in one cell line some low level expression of AAV Rep52 protein but no Rep78 or Rep68 protein after stable transfection of HeLa or 293 cells with plasmids containing an AAV rep gene. Because of the absence of Rep78 and Rep68 proteins, vector could not be produced in the cell line. Another cell line made a barely detectable amount of Rep78 which was nonfunctional.

Vincent et al. (1990, Vaccines 90, Cold Spring Harbor Laboratory Press, pp. 353–359) attempted to generate cell lines containing the AAV rep and cap genes expressed from the normal AAV promoters, but these attempts were not successful either because the vectors were contaminated with a 100-fold excess of wild-type AAV particles or because the vectors were produced at only very low titers of less than 4×10³ infectious particles.

Other variations that have been proposed include systems based on the production of AAV Cap proteins that might be used to reconstitute AAV particles, e.g. by assembly in vitro (see, e.g., WO 96/00587, published Nov. 1, 1996); systems employing AAV rep-cap genes on a helper virus (see, e.g., WO 95/06743, published Mar. 9, 1995); and systems employing helper viruses from non-human mammals (see, e.g., WO 95/20671, published Aug. 3, 1995).

In yet another approach, Lebkowski et al. (U.S. Pat. No. 5,173,414, issued Dec. 22, 1992) constructed cell lines containing AAV vectors in an episomal plasmid. These cell lines could then be infected with adenovirus and transfected with the trans-complementing AAV functions rep and cap to generate preparations of AAV vector. It is claimed that this allows higher titers of AAV stocks to be produced. However, in the examples described, the only information relative to titer that is shown is that one human cell line, K562, could be transduced at efficiencies of only 1% or less, which does not indicate high titer production of any AAV vector. In this system the vector is carried as an episomal (unintegrated) construct, and it is stated that integrated copies of the vector are not preferred. In a subsequent patent (U.S. Pat. No. 5,354,678, issued Oct. 11, 1994), Lebkowski et al. suggest introducing rep and cap genes into the cell genome but the method again requires the use of episomal AAV transducing vectors comprising an Epstein-Barr virus nuclear antigen (EBNA) gene and an Epstein-Barr virus latent origin of replication; and, again, the only information relative to titer indicated that it was fairly low. Similarly, Kotin et al. (WO95/14771, published Jun. 1, 1995) suggested a system employing "first" and "second" vectors to provide a source of an rAAV vector and AAV rep-cap genes, respectively. The proposed system involves a series of sequential transfections/infections of the host cells, in a transient transfection system. No data were provided regarding rAAV viral titers obtained and, indeed, it is not apparent that any rAAV virus was actually produced according to the suggested system, much less at high titer).

The problem of suboptimal levels of rep expression after plasmid transfection also relates to another biological activity of these proteins. There is evidence (Tratschin et al., 1986, Mol. Cell. Biol. 6:2884–2894) that AAV Rep proteins down-regulate their own expression from the AAV-p5 promoter which has been used in the various previously described packaging constructs such as pAAV/Ad (Samulski et al., 1989) or pBa1A (Lebkowski et al., 1988, 1992).

Another attempt to develop cell lines expressing functional rep activity was recently published by Hölscher et al. (1994, J. Virol. 68:7169–7177). They described the generation of cell lines in which rep was placed under control of a glucocorticoid-responsive MMTV promoter. Although they observed particle formation, the particles were apparently noninfectious. Additional experiments indicated that the defect was quite fundamental; namely, there was virtually no accumulation of single-stranded rAAV DNA in the cells. Production of infectious particles required an additional transient transfection with constitutive highly-expressed rep constructs (i.e. they had to "add back" Rep activity to cells that were supposed to be able to provide it themselves).

There is a significant need for methods that can be used to efficiently generate rAAV vectors that are essentially free of wild-type or other replication-competent AAV; and a corresponding need for cell lines that can be used to effectively generate such rAAV vectors. Several improved approaches to generating AAV packaging cell lines have also been described recently, see, e.g., T. Flotte et al., WO 95/13365 (Targeted Genetics Corporation and Johns Hopkins University), and corresponding U.S. Pat. No. 5,658, 776; J. Trempe et al., WO 95/13392 (Medical College of Ohio), and corresponding U.S. patent application Ser. No. 08/362,608, now issued as U.S. Pat. No. 5,837,484; and J. Allen, WO 96/17947 (Targeted Genetics Corporation). The present invention provides additional improvements in the production of high-titer rAAV vector preparations.

DISCLOSURE OF THE INVENTION

The present invention provides compositions and methods that provide amplifiable expression of the AAV rep and/or cap genes (also referred to herein as "AAV packaging genes") which can be employed in the generation of recombinant AAV (rAAV) vectors. In particular, the inventors have found that by removing the AAV rep and/or cap genes from their normal environment (i.e. flanked by the AAV ITRs) and placing them in amplifiable linkage with one or more activating elements (exemplified by the "P1" sequence of human chromosome 19, or analogous elements), it is possible to obtain controlled but highly amplifiable expression of the AAV packaging genes in cells to be used for the preparation of rAAV vectors. As described and exemplified herein, packaging cassettes comprising rep and/or cap sequences in amplifiable linkage to P1 or a P1-like element can be integrated into the chromosome of a host cell or can be maintained extrachromosomally as an episome. The methods and compositions of the present invention can be used to generate stable AAV producer cells that are capable of supporting production of a very large burst of rAAV particles upon infection with a suitable helper virus (such as adenovirus) or provision of helper functions.

Accordingly, in one embodiment, the invention provides a recombinant polynucleotide sequence encoding an adeno-associated virus (AAV) packaging cassette comprising at least one AAV packaging gene amplifiably linked to a P1 sequence, or an equivalent activating element.

In additional embodiments, the invention provides methods for producing high-titer stocks of rAAV vectors containing a foreign gene of interest, by co-expressing an rAAV vector containing a gene of interest along with an AAV packaging cassette comprising at least one AAV packaging gene amplifiably linked to an activating element.

The invention also provides compositions and methods for producing cell lines comprising an AAV packaging cassette of the invention together with an rAAV vector containing a gene of interest; cell lines produced thereby; compositions and methods for high-efficiency packaging of an rAAV vector containing a gene of interest; and rAAV vectors packaged according to the method of the invention.

As illustrated below, AAV packaging cassettes comprising one or more activating elements and one or more AAV packaging genes can be introduced into a host cell and propagated episomally or they can be integrated into a chromosome of a mammalian host cell. Thus, in an exemplary embodiment, the invention provides AAV packaging cassettes comprising AAV packaging genes and an activating element that are capable of integrating into the genome of a host cell (such as a mammalian cell); as well as packaging cells comprising such stably-integrated integrated cassettes. In another exemplary embodiment, the invention provides episomal packaging cassettes comprising one or more AAV packaging genes and one or more activating elements, present within a host cell as a freely-replicating episome (or capable of being introduced into a host cell such that, after introduction into the host cell, the packaging cassette will exist as a freely-replicating episomal element); as well as packaging cells comprising such episomally-maintained packaging cassettes. Illustrative examples of the design and use of both types are provided herein.

DETAILED DESCRIPTION OF THE INVENTION

Figure 1:
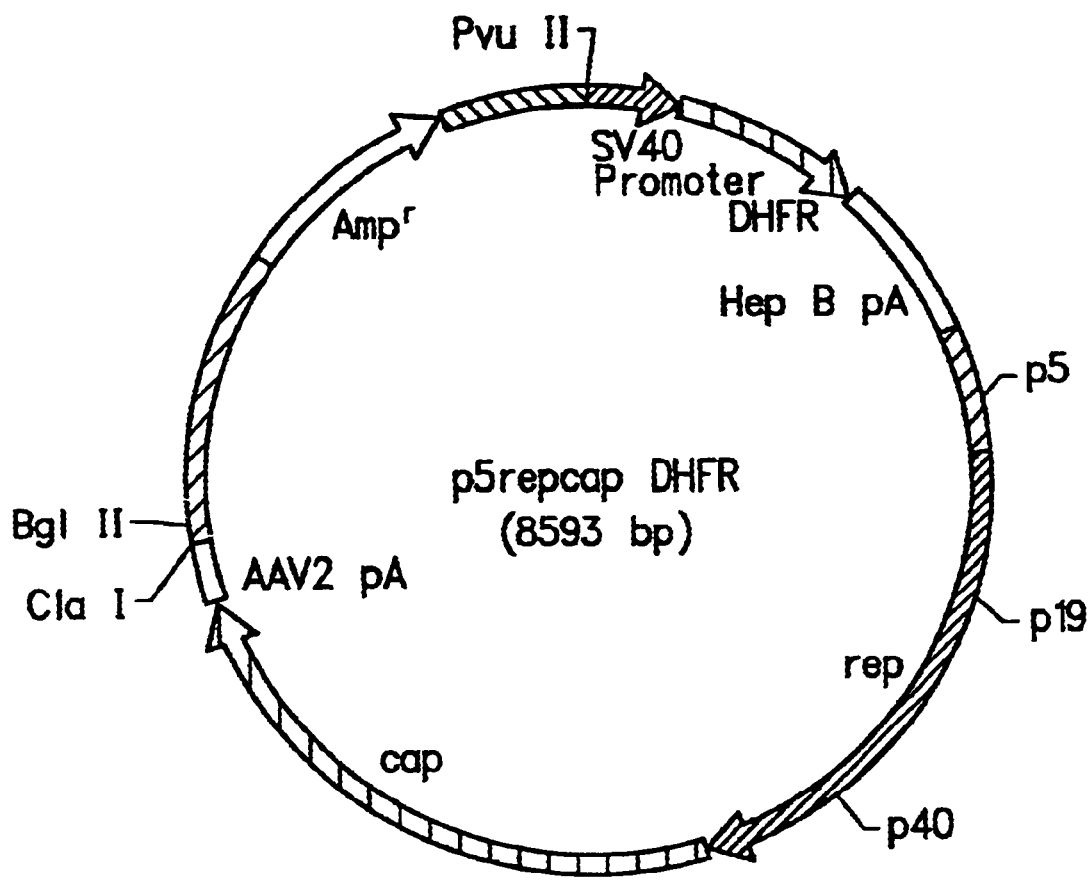
FIG. 1 shows a map of the p5repcapDHFR plasmid.

A basic challenge in the area of gene therapy is the development of strategies for efficient gene delivery to cells and tissues in vivo. One strategy involves the use of adeno-associated virus (AAV) vectors. Recombinant AAV vectors are recombinant constructs of the AAV genome comprising sequences required in cis for vector packaging (typically AAV ITR sequences), along with heterologous polynucleotide(s) encoding a protein or function of interest. Recombinant AAV vectors are potentially powerful tools for human gene therapy.

Although rAAV vectors are capable of in vivo gene delivery, for example in the respiratory tract, high titers of such vectors are necessary to allow the delivery of a sufficiently high multiplicity of vector in a minimal volume. Consequently, optimal packaging methodology is of central importance for AAV-mediated gene therapy approaches. Packaging of rAAV vectors is mediated by the products of two AAV genes: rep (replication proteins) and cap (capsid proteins), which can be provided separately in trans. A sequence comprising AAV packaging genes to be provided in trans is often referred to herein as a "packaging cassette". It is thus desirable to construct packaging cell lines containing both the AAV packaging genes (e.g., in a packaging cassette) and an rAAV vector. However, stable, helper-free AAV packaging cell lines have been difficult to obtain, primarily due to the activities of Rep and Cap proteins, for which low-level expression can impose a severe constraint on packaging, while high-level expression (particularly of Rep proteins) can negatively affect the host cell (see Background). The present invention provides controlled but amplifiable expression of the rep and cap genes, to thereby provide Rep and capsid proteins at levels sufficient for production of high-titer vector stocks, while avoiding any effects of cell toxicity (as can occur if the rep gene is placed under the control of regulatory elements that exhibit some constitutive activity or are not tightly regulated).

The methods and compositions of the present invention, which allow for controlled, amplifiable expression of AAV packaging genes, even when the packaging genes are expressed from their native promoters (such as the rep gene p5 promoter, which is a relatively weak promoter), provide substantial improvements in packaging efficiency. This is accomplished by providing AAV packaging genes in a recombinant DNA construct wherein they are amplifiably linked to an activating element. In preferred embodiments, the activating element is directly or indirectly triggered by the user when it is desired to initiate vector production, preferably by infection with helper virus or provision of helper function. The use of the P1 sequence of human chromosome 19 is exemplary in these respects. Thus, in the absence of adenovirus infection (or equivalent helper function), little if any Rep is produced from the p5 promoter, which is relatively weak or inactive in the absence of helper virus infection or provision of helper function (e.g., adenovirus infection or inclusion in the host cells of helper functions, such as E1A activity in human 293 cells). Without wishing to be bound by theory, it appears that upon infection or provision of helper function, the p5 promoter is turned on to some degree, resulting in the synthesis of some Rep protein, which may then, by acting via the P1 activating element, trigger an amplification event by which the linked rep and/or cap genes are amplified—thereby serving as the basis for a much higher level of expression. The activating element, exemplified by P1, can thus promote amplification of AAV packaging genes to which it is linked. The resulting elevation in template levels would allow the gene products (like Rep and Cap proteins) to be produced in much higher amounts, particularly in view of the fact that their promoters can also be transcriptionally activated to thereby provide efficient packaging functions. Inclusion of an activating element in an AAV packaging cassette, along with AAV packaging genes, thus provides a new type of AAV packaging cassette which is particularly useful in the production of high-titer stocks of rAAV vectors, as described and exemplified herein.

Some previous attempts to incorporate rep genes into a host cell may have resulted in either of two undesirable alternatives: (1) host cells containing a stably-integrated, expressed rep gene in which cytotoxic and/or cytostatic effects limit cell growth and/or led to poor titers of rAAV vectors; or (2) host cells exhibiting normal growth rates, but nevertheless having little capability for generating high titers of rAAV vectors (possibly reflecting integration at transcriptionally silent sites, sequence rearrangements, etc.). Without wishing to be bound by theory, it is proposed that the AAV packaging cassettes of the present invention can also be used to effectively provide a baseline level of Rep proteins that is very low (if present at all) and is therefore not detrimental to the growth of the host cell, but can be amplified when required (for example by helper virus infection or provision of helper function) to a level that promotes efficient production of rAAV vectors. Thus, when brought about under the control of the user, amplification results in increased levels of templates comprising AAV packaging genes, which collectively allow high levels of expression of packaging gene products (e.g., Rep and Cap proteins), which in turn facilitates production of high titers of rAAV genomes.

In the case of the wild-type AAV, for example, it is generally believed that the native promoter for Rep protein expression (p5) is relatively weak and consequently that synthesis of native Rep proteins does not occur to any substantial degree in the absence of stimulatory factors such as the E1A proteins provided by adenovirus as a helper virus, or equivalent helper functions. (It should be noted that human 293 cells contain portions of the human adenovirus genome, in particular the E1 region, that appear to stimulate the p5 promoter.) In addition to the relatively low activity of the rep p5 promoter in the absence of helper function, it appears that AAV Rep proteins can effectively modulate their own expression. Both of these phenomena tend to prevent replication from occurring when the virus is in the latent proviral state.

The present invention effectively provides for controlled amplification of DNA comprising the packaging cassettes of the invention, thereby providing increased template levels for synthesis of AAV packaging proteins. Thus, in the packaging cassettes of the invention, AAV packaging genes can be operably linked to relatively weak promoters and nevertheless be capable of providing acceptable levels of packaging proteins upon activation. In preferred embodiments, AAV packaging genes are operably linked to their native promoters (i.e., p5, p19 and p40, in the case of AAV2 as described above). Since p5 is an extremely weak promoter, and virtually no transcription initiated from p5 is observed in the absence of helper function, an AAV packaging cassette wherein packaging gene expression is controlled by p5 is not likely to have any Rep-dependent cytostatic effect on the host cell prior to activation and amplification. However, upon activation by helper virus infection or provision of helper function, the packaging cassette template is amplified, leading to a greater number of templates for transcription of AAV packaging proteins. Furthermore, helper virus infection or provision of helper function is believed also to stimulate transcription from the p5 promoter (which regulates synthesis of mRNA encoding Rep proteins). Accordingly, in the packaging cassettes of the invention, expression of AAV packaging genes is preferably not triggered until provision of helper function (i.e., at the time the host cells are to be used for packaging of rAAV particles), thereby avoiding the accumulation of high (and potentially cytostatic or cytotoxic) levels of AAV packaging proteins prior to the time they are required for packaging. These preferred embodiments thus provide two levels of augmentation of packaging protein synthesis, in which a helper function-dependent activating element is amplifiably linked to sequences encoding AAV packaging genes, whose promoters are also stimulated by helper function.

The inventors have shown, as described below, that AAV packaging cassettes comprising activating elements (as exemplified by the P1 sequence element) can be used to generate dramatic increases in the levels of vector production. The use of P1 sequences as activating elements for the AAV packaging cassettes of the present invention is believed to be particularly convenient since the same event that is required to trigger the productive generation of AAV particles (i.e. provision of helper virus or helper functions) is believed to also trigger amplification of a construct containing an activating element such as P1 (such as, for example, a packaging cassette of the invention), and up-regulate the AAV promoters (including P5), resulting in both provision of increased template and in higher levels of synthesis of the packaging gene products (i.e. AAV packaging proteins) from the amplified templates. Thus, according to the present invention, the coupling of activating elements, such as P1, with AAV packaging genes can provide a combination of advantages including control of packaging gene product levels (in the "pre-activated" state) and, upon activation, amplification of template levels and stimulation of transcription.

It is also noted that, in many cases, the activation of replication origins is, or can be, subject to strict control. Accordingly, various replication origins, such as those present in eukaryotic or prokaryotic chromosomes, viral genomes, organelle genomes, and bacteriophage genomes, for example, and other origin-like or "ori-like" sequences can be used in the practice of the invention (e.g., as alternatives or additions to the use of P1). Such "activatable" origins are those that are not constitutive, but rather require a signal before replication initiation and subsequent amplification of linked sequences will occur.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, *Molecular Cloning: A Laboratory Manual*, Second Edition (1989); *Oligonucleotide Synthesis* (M. J. Gait Ed., 1984); *Animal Cell Culture* (R. I. Freshney, Ed., 1987); the series *Methods in Enzymology* (Academic Press, Inc.); *Gene Transfer Vectors for Mammalian Cells* (J. M. Miller and M. P. Calos eds. 1987); *Handbook of Experimental Immunology*, (D. M. Weir and C. C. Blackwell, Eds.); Current Protocols in Molecular Biology (F. M. Ausubel, R. Brent, R. E. Kingston, D. D. Moore, J. G. Seidman, J. A. Smith, and K. Struhl, eds., 1987); and Current Protocols in Immunology (J. E. Coligan, A. M. Kruisbeek, D. H. Margulies, E. M. Shevach and W. Strober, eds., 1991).

All patents, patent applications, and publications mentioned herein, both supra and infra, are hereby incorporated herein by reference.

Definitions

The terms "polypeptide", "peptide" and "protein" are used interchangeably to refer to polymers of amino acids of any length. These terms also include proteins that are post-translationally modified through reactions that include, but are not limited to, glycosylation, acetylation and phosphorylation.

"Polynucleotide" refers to a polymeric form of nucleotides of any length, either ribonucleotides or deoxyribonucleotides, or analogs thereof. This term refers only to the primary structure of the molecule. Thus, double- and single-stranded DNA, as well as double- and single-stranded RNA are included. It also includes modified polynucleotides such as methylated or capped polynucleotides.

A "gene" refers to a polynucleotide containing at least one open reading frame that is capable of encoding a particular protein after being transcribed and translated.

A "transcriptional regulatory sequence" as used herein, refers to a nucleotide sequence that controls the transcription of a gene or coding sequence to which it is operably linked. Transcriptional regulatory sequences of use in the present invention generally include at least one transcriptional promoter and may also include one or more enhancers and/or terminators of transcription.

A "promoter," as used herein, refers to a nucleotide sequence that directs the transcription of a gene or coding sequence to which it is operably linked.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the transcriptional regulatory sequence or promoter promotes transcription of the coding sequence. An operably linked transcriptional regulatory sequence is generally joined in cis with the coding sequence, but it is not necessarily directly adjacent to it.

"Recombinant," refers to a genetic entity distinct from that generally found in nature. As applied to a polynucleotide or gene, this means that the polynucleotide is the product of various combinations of cloning, restriction and/or ligation steps, and other procedures that result in a construct that is distinct from a polynucleotide found in nature.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a transcriptional regulatory sequence or promoter that is removed from its native coding sequence and operably linked to a different coding sequence is a heterologous transcriptional regulatory sequence or promoter.

A "vector", as used herein, refers to a recombinant plasmid or virus that comprises a polynucleotide to be delivered into a host cell, either in vitro or in vivo. The polynucleotide to be delivered, sometimes referred to as a "target polynucleotide," "transgene", or "gene of interest" may comprise a coding sequence of interest in gene therapy (such as a gene encoding a protein of therapeutic interest) and/or a selectable or detectable marker.

A "replicon" refers to a polynucleotide comprising an origin of replication which allows for replication of the polynucleotide in an appropriate host cell. Examples of replicons include episomes (including plasmids), as well as chromosomes (such as the nuclear or mitochondrial chromosomes).

An "origin," "replication origin," "ori-like sequence" or "ori element" is a nucleotide sequence involved in one or more aspects of initiation of DNA replication, such as, for example, binding of replication initiation factors, unwinding of the DNA duplex, primer formation, and/or template-directed synthesis of a complementary strand. As discussed in detail herein and in the art, ori-like sequences can generally be found in any polynucleotide that is naturally replicated, including plasmids and viruses, as well as prokaryotic, mitochondrial and chloroplast genomes and eukaryotic chromosomes. Such ori-like sequences can be identified genetically (i.e., replication-defective mutants, ars sequences) or functionally (i.e., through biochemical assay, electron microscopy, etc.), as is known in the art.

"Stable integration" of a polynucleotide into a cell means that the polynucleotide has been integrated into a replicon that tends to be stably maintained in the cell. Although episomes such as plasmids can sometimes be maintained for many generations, genetic material carried episomally is generally more susceptible to loss than chromosomally-integrated material. However, maintenance of a polynucleotide can often be effected by incorporating a selectable marker into or adjacent to a polynucleotide, and then maintaining cells carrying the polynucleotide under selective pressure. In some cases, sequences cannot be effectively maintained stably unless they have become integrated into a chromosome; and, therefore, selection for retention of a sequence comprising a selectable marker can result in the selection of cells in which the marker has become stably-integrated into a chromosome. Antibiotic resistance genes can be conveniently employed as such selectable markers, as is well known in the art. Typically, stably-integrated polynucleotides would be expected to be maintained on average for at least about twenty generations, preferably at least about one hundred generations, still more preferably they would be maintained permanently. The chromatin structure of eukaryotic chromosomes can also influence the level of expression of an integrated polynucleotide. Having the genes carried on stably-maintained episomes can be particularly useful where it is desired to have multiple stably-maintained copies of a particular gene. The selection of stable cell lines having properties that are particularly desirable in the context of the present invention are described and illustrated below.

"AAV" is adeno-associated virus. Adeno-associated virus is a defective parvovirus that grows only in cells in which certain functions are provided by a co-infecting helper virus. General reviews of AAV may be found in, for example, Carter, 1989, *Handbook of Parvoviruses*, Vol. I, pp. 169–228, and Berns, 1990, *Virology*, pp. 1743–1764, Raven Press, (New York). The AAV2 serotype was used in some of the illustrations of the present invention that are set forth in the Examples. However, it is fully expected that these same principles will be applicable to other AAV serotypes since it is now known that the various serotypes are quite closely related—both functionally and structurally, even at the genetic level (see, e.g., Blacklow, 1988, pp. 165–174 of *Parvoviruses and Human Disease*, J. R. Pattison (ed.); and Rose, 1974, *Comprehensive Virology* 3: 1–61). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to inverted terminal repeats (ITRs). The similar infectivity patterns also suggest that the replication functions in each serotype are under similar regulatory control.

A "recombinant AAV vector" (or "rAAV vector") refers to a vector comprising one or more polynucleotide sequences of interest, genes of interest or "transgenes" that are flanked by AAV inverted terminal repeat sequences (ITRs). Such rAAV vectors can be replicated and packaged into infectious viral particles when present in a host cell that has been infected with a suitable helper virus and that is expressing AAV rep and cap gene products (i.e. AAV Rep and Cap proteins). When an rAAV vector is incorporated into a larger polynucleotide (e.g. in a chromosome or in another vector such as a plasmid used for cloning or transfection), then the rAAV vector is typically referred to as a "pro-vector" which can be "rescued" by replication and encapsidation in the presence of AAV packaging functions and necessary helper functions.

A "helper virus" for AAV refers to a virus that allows AAV (which is a "defective" parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC. "Helper function" refers to the activity provided by the helper virus that allows replication and packaging of an AAV genome, or any equivalent activity. Helper functions are also believed to stimulate transcription of some AAV promoters, including p5, and may enhance processivity of replication in cells in which helper functions are expressed.

"Packaging" as used herein refers to a series of subcellular events that results in the assembly and encapsidation of a viral vector, particularly an rAAV vector. Thus, when a suitable vector is introduced into a packaging cell line under appropriate conditions, it can be assembled into a viral particle. Functions associated with packaging of viral vectors, particularly rAAV vectors, are described herein and in the art.

AAV "rep" and "cap" genes are genes encoding replication and encapsidation proteins, respectively. AAV rep and cap genes have been found in all AAV serotypes examined, and are described herein and in the references cited. In wild-type AAV, the rep and cap genes are generally found adjacent to each other in the viral genome (i.e. they are "coupled" together as adjoining or overlapping transcriptional units), and they are generally conserved among AAV serotypes. AAV rep and cap genes are also individually and collectively referred to herein as "AAV packaging genes." AAV packaging genes that have been modified by deletion or point mutation, or which have been subdivided into components which can be rejoined by recombination (e.g., as described in co-owned U.S. patent application Ser. No. 60/041,609, filed Dec. 18, 1996, the disclosure of which is hereby incorporated by reference), may also be used in the present invention. AAV packaging genes can also be operably linked to other transcriptional regulatory sequences, including promoters, enhancers and polyadenylation ("polyA") sequences (which additional transcriptional regulatory sequences can also be heterologous). An "AAV packaging cassette" is a recombinant construct which includes one or more AAV packaging genes.

"Efficiency" when used in describing a cell line refers to certain useful attributes of the line; in particular, the growth rate, and (for packaging cell lines) the number of virus particles produced per cell. "Efficient growth" of a packaging cell line refers to the effective growth rate of the packaging cell, related to a comparable parental-type cell (i.e., a cell that does not carry an introduced AAV packaging gene) Preferably, the relative growth rate is at least 20% of the parental type, more preferably, 40%, more preferably, 80%, still more preferably, 90% and, most preferably, 100%. "High efficiency packaging" indicates production of at least about 100 viral particles per cell, more preferably at least about 1,000 viral particles per cell, still more preferably at least about 10,000 viral particles per cell. "High safety packaging" indicates that, of the recombinant AAV viral particles produced, fewer than about 1 in $10^6$ are replication-competent AAV viral particles, preferably fewer than about 1 in $10^8$ are replication-competent, more preferably fewer than about 1 in $10^{10}$ are replication-competent, still more preferably fewer than about 1 in $10^{12}$ are replication-competent, most preferably none are replication-competent. Preferred packaging cells of the present invention exhibit combinations of such high efficiency and high safety.

"Host cells", "cell lines", "cell cultures", "packaging cell line" and other such terms denote higher eukaryotic cells, preferably mammalian cells, most preferably human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene", "target polynucleotide", "transgene", "gene of interest" and the like generally refer to a gene or genes to be transferred using a vector. Typically, in the context of the present invention, such genes are located within the rAAV vector (which vector is flanked by inverted terminal repeat (ITR) regions and thus can be replicated and encapsidated into rAAV particles). Target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; (vi) polynucleotides for cancer therapy, such as E1A tumor suppressor genes or p53 tumor suppressor genes for the treatment of various cancers and (vii) polynucleotides that encode antigens or antibodies. To effect expression of the transgene in a recipient host cell, it is preferably operably linked to a promoter or other such transcriptional regulatory sequence, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rAAV vector may also contain a selectable marker.

An "activating element" is a sequence that responds to the presence of an activation signal by amplifying (i.e., replicating the sequences) to which it is amplifiably linked. A preferred activating element is the P1 element and preferred activation signals include AAV helper functions (as exemplified by adenovirus E1A function) or their equivalents. As used herein, two sequences, one of which is an activating element, are "amplifiably linked" when they are in sufficient proximity to each other that replication initiating from the activating element results in amplification (i.e., increased copy number) of the other sequence. Preferably, the copy number of the amplified sequence is amplified 2-fold or greater, more preferably, 10-fold or greater, still more preferably, 20-fold or greater. It is to be noted that the ability of an activating element to amplify an amplifiably-linked sequence will be influenced by the degree of processivity of replication initiating from the activating element. Thus, factors that enhance processivity of replication will tend to increase the effective level of amplification of a sequence that is amplifiably linked to an activating element. In the context of the present invention, infection with adenovirus, or provision of equivalent helper function, may enhance processivity of replication as well as initiating amplification.

Sequences Activating Amplification and Controlled, High-efficiency Expression of AAV Packaging Genes The present inventors have discovered that activating elements such as the P1 sequence (normally found on human chromosome 19), when amplifiably linked to AAV packaging genes, can provide controlled, amplifiable expression of the linked packaging genes and/or a dramatic increase in the ability of such genes to support the production of high titers of rAAV vectors. In particular, when an AAV packaging cassette of the present invention is co-expressed in host cells with an rAAV vector (containing one or more genes of interest flanked by AAV ITR sequences) under suitable conditions including the provision of helper virus or helper function, high titers of AAV virus containing the rAAV vector are produced by the host cells. Thus, P1 exemplifies a class of activating elements possessing, among other properties, activatable replication function, that is useful in the construction of AAV packaging cassettes to promote production of high-titer stocks of rAAV vectors.

The methods and compositions of the invention will therefore utilize recombinant DNA constructs wherein AAV packaging genes are amplifiably linked to one or more activating elements. The presently preferred activating elements are exemplified by P1 and P1-like elements that exhibit structural and functional properties related to initiation of replication. Most preferred are elements that act as helper function-inducible origins of replication. Other sequences that can be directly or indirectly induced to initiate replication in response to helper function will also be useful in the practice of the invention. In addition, sequences that are not inducible by helper function, but which can be induced to initiate DNA replication by other stimuli (provided and/or controlled by the user), are also useful as activating elements in the practice of the invention. Examples of such other inducible activating elements would include, by way of illustration, a sequence at which replication is initiated in the presence of a replication protein that is itself inducible (e.g., a temperature-sensitive replication protein that can be activated by a shift to permissive temperature, or a replication protein whose gene is placed under the control of an inducible promoter). Naturally-occurring activating elements having the desired properties can be isolated; alternatively, synthetic sequences can be designed based, in whole or in part, on the observed relationships between structure and function found in naturally-occurring activating elements.

The P1 element contains at least two distinct sequence motifs, a site at which Rep proteins can bind, known as the "Rep-binding motif" (or "Rep-binding site") and a terminal resolution site, at which bound Rep protein can nick the DNA (see Example A 1). During AAV replication, it is believed that Rep protein binds within the AAV inverted terminal repeat and catalyzes the formation of a nick (at the terminal resolution site), resulting in covalent attachment of Rep protein to the newly generated 5' end. The 3' end of the nick serves as a primer for AAV DNA synthesis. Consequently, the Rep binding motif and/or the terminal resolution sequence, alone or in combination, may form all or part of an activating element for expression of AAV packaging genes. Furthermore, binding and cleavage of a sequence by Rep proteins can be used as an assay to identify additional activating elements.

With respect to the use of inducible origins as activating elements, it is noted that origin sequences in eukaryotes ("ori sequences") are generally associated with several characteristic functions including, but not limited to, protein binding, DNA unwinding and template-directed chain elongation. See, for example, Kornberg and Baker (1992) DNA REPLICATION, Second Edition, W. H. Freeman & Co., New York; Boulikas (1996) *J. Cell Biochem.* 60:297–316; and Diffley (1996) *Genes & Devel.* 10:2819–2830. Accordingly, sequences having one or any combination of these properties can find use as activating elements in the practice of the present invention.

For instance, various initiator proteins bind at or near the ori sequence to facilitate initiation of DNA replication. Accordingly, sequences capable of binding such initiator proteins, and the initiator proteins themselves (and their encoding genes) can find use in the practice of the invention. Determination of the ability of a particular protein to bind to an ori sequence can be assayed by several methods that are well-known in the art, including, but not limited to, sedimentation, nuclease protection, filter binding, gel mobility-shift, and various affinity techniques, including, but not limited to, DNA affinity matrices. Assays for origin function are well-known in the art and include electron microscopy, genetic analysis and template-directed incorporation of labeled nucleoside triphosphate, to name just a few. Activation of origin function can be detected as an increase in level of replication as determined by the above-mentioned origin assays. Thus, origin sequences can be identified, proteins that interact with a particular origin can also be identified, and the ability of an ori-binding protein to activate a particular origin can be determined by methods that are well-known in the art.

Thus, in additional embodiments, activating elements can take the form of inducible replication origins, such as mammalian, viral, mitochondrial, chloroplast, plasmid or bacteriophage replication origins, for example.

Accordingly, an inducible origin can be amplifiably linked to AAV packaging genes in an AAV packaging cassette and the packaging cassette can be introduced into suitable host cells containing an rAAV vector (or to which an rAAV vector is added simultaneously or subsequently). When packaging of the rAAV vector is required, the host cells are provided with a molecule, such as a protein, which activates the inducible origin, along with a helper function. The activating molecule can be provided directly. Alternatively, if the activating molecule is a protein, then a gene (or genes) encoding the protein, under the transcriptional control of an inducible promoter, can be present in the host cells. In this case stimulation of transcription of the gene(s) encoding the activating protein can be achieved by provision of the appropriate inducing molecule, or the gene(s) encoding the activating protein can be placed under the control of a promoter that is activated by a helper function, such as adenovirus infection. An appealing feature of the latter method is that the same signal (i.e., provision of helper function) can be responsible for transcriptional stimulation of both the gene(s) encoding the inducing molecule(s) and AAV packaging genes (since, for instance, transcription from the p5 promoter is thought to be stimulated by helper function, such as adenovirus infection). For additional, non-limiting examples of promoters that are inducible by helper function (and methods to identify such promoters) see, for example, co-owned PCT Publication WO 96/17947, the disclosure of which is hereby incorporated by reference in its entirety. Further examples of inducible promoters include, but are not limited to, the MMTV LTR promoter, which is inducible by glucocorticoids, and the metallothionein promoter, which is inducible by heavy metals. Many other inducible promoters are known in the art and can be used in this aspect of the invention.

Among other sequence that are commonly associated with origins of replication are palindromic sequences, sequences having the potential to form cruciform structures, DNA unwinding elements, sequences involved in synthesis or recruitment of replication primers, bent or curved DNA (which can be detected by its altered electrophoretic mobility), nuclease sensitive sequences, and nuclear matrix attachment sites. See, for example, Boulikas (1996) *J. Cell Biochem.* 60:297–316; and Diffley (1–996) *Genes & Devel.* 10:2819–2830. In addition, sequences involved in chromosomal or extrachromosomal gene amplification can also be used as activating elements. To provide just one example, amplification of the dihydrofolate reductase (DHFR) gene occurs in response to methotrexate.

Sequences possessing origin activity, which may be useful as activating elements, can also be identified by electron microscopic analysis of replicating DNA molecules. See, for example, Fareed et al. (1980) *Meth. Enzymology*, vol. 65 (eds. L. Grossman and K. Moldave), Academic Press, New York, pp. 709–717.

Assays for ori-like sequences that can serve as activating elements in the present invention have been described above and are well-known to those of skill in the art. In addition, proteins, such as Rep, which interact with particular activating elements, can be identified by methods well-known in the art, including those described above, and used for the identification of additional activating elements.

Orientation and Spacing of Activating Elements With Respect to AAV Packaging Genes We have observed that placing an activating element, as exemplified by a P1 sequence, near to a cassette comprising AAV packaging genes resulted in a dramatic increase in the ability of the packaging genes to support the production of recombinant AAV vectors. Indeed, as shown below, a P1 element placed more than 4 kb downstream of the rep gene transcriptional start site in an integrated AAV packaging cassette resulted in approximately a 14-fold amplification of the packaging cassette (see Example A 11 below) and close to a 1,000-fold increase in rAAV virus titer (see Example A 12 below), compared to cells containing a packaging cassette lacking a P1 element. Although placing an activating element further away from an AAV packaging gene (e.g. 5–10 kb or further) may result in somewhat lower activity, longer distances between an activating element and its amplifiably-linked AAV packaging genes would still be expected to provide a degree of activation sufficient for improved rAAV production, especially under conditions in which processivity of replication is enhanced, as discussed above. Where P1 is used as an activating element, it can be desirable to have at least some spacer sequence(e.g. about 0.5 to 1 kb) between the P1 sequence and the AAV packaging genes in order to reduce or eliminate the possibility that recombination between P1 and an ITR sequence could regenerate a replication-competent AAV genome that would be of a size that could be efficiently packaged.

In amplifying copies of integrated AAV in response to helper virus infection, the P1 element appears to direct amplification unidirectionally. Without wishing to be bound by theory, it is believed that interaction of Rep with a Rep-binding motif may be followed by nicking between the two T residues in a Terminal Resolution Site (TRS), as illustrated below. Subsequently, replication may initiate from the 3' hydroxyl end of the nick and proceed toward the Rep-binding motif. Accordingly, it is presently preferred that a unidirectional activating element as in the case of P1 be oriented such that unidirectional replication proceeds from the activating element toward the associated AAV packaging gene(s). Alternatively, AAV packaging genes can be flanked by activating elements that are oriented so that replication initiated at each element proceeds "inward" toward the AAV packaging gene(s). However, bidirectional activating elements are also useful in the practice of the invention, since, in these cases, one of the two directions of replication will proceed toward the associated AAV packaging genes. Furthermore, for episomal packaging cassettes, a unidirectional activating element wherein replication is oriented away from associated AAV packaging genes can also be useful, since replication will proceed around the circular episomal genome and eventually encounter the associated AAV packaging gene sequences. One can also incorporate multiple copies of such activating elements, which can be oriented to promote replication in both directions. Exemplary illustrations of such constructs are provided below.

Addition of multiple activating elements to an AAV packaging cassette would be expected to provide further degrees of amplification. For example, two P1 elements that are oriented such that replication initiated from each progresses in opposite directions would provide correspondingly higher levels of amplification of linked sequences. Thus, insertion of a second P1 element into a construct such as P1 RCD in such an orientation as to amplify the opposite strand of an integrated packaging construct should increase amplification, Rep and Cap levels and rAAV virus production.

In general, addition of multiple activating elements to the AAV packaging cassettes of the invention should increase amplification and therefore should increase levels of AAV packaging gene products. Consequently, production of rAAV vectors and virus production should also be increased under these conditions, compared to situations in which a single activating element is present in a packaging cassette.

Production of rAAV Vectors

To generate recombinant AAV particles useful for such purposes as gene therapy, the packaging cell line is generally supplied with a recombinant AAV vector comprising AAV inverted terminal repeat (ITR) regions surrounding one or more polynucleotides of interest (or "target" polynucleotides).

The target polynucleotide, if it is intended to be expressed, is generally operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rAAV vector can also contain a positive selectable marker in order to allow for selection of cells that have been infected by the rAAV vector; and/or a negative selectable marker (as a means of selecting against those same cells should that become necessary or desirable); see, e.g., S. D. Lupton, PCT/US91/08442 and PCT/US94/05601.

By way of illustration, we have used rAAV vectors containing polynucleotides that encode a functional cystic fibrosis transmembrane conductance regulator polypeptide (CFTR) operably linked to a promoter. As is now known in the art, there are a variety of CFTR polypeptides that are capable of reconstituting CFTR activity in cells derived from cystic fibrosis patients. For example, Carter et al. have described truncated variants of CFTR genes that encode functional CFTR proteins (see, e.g., U.S. Ser. No. 08/455, 552, filed May 31, 1995, now proceeding to issuance). See also, Rich et al. (1991, Science, 253: 205–207) who have described a CFTR derivative missing amino acid residues 708–835, that was capable of transporting chloride and capable of correcting a naturally occurring CFTR defect, and Egan et al. (1993) who described another CFTR derivative (comprising about 25 amino acids from an unrelated protein followed by the sequence of native CFTR beginning at residue 119) that was also capable of restoring electrophysiological characteristics of normal CFTR. To take two additional examples, Arispe et al. (1992, Proc. Natl. Acad. Sci. USA 89: 1539–1543) showed that a CFTR fragment comprising residues 433–586 was sufficient to reconstitute a correct chloride channel in lipid bilayers; and Sheppard et al. (1994, Cell 76: 1091–1098) showed that a CFTR polypeptide truncated at residue 836 to about half its length was still capable of building a regulated chloride channel. Thus, the native CFTR protein, and mutants and fragments thereof, all constitute CFTR polypeptides that are useful in the practice of this invention.

Other useful target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as the wild-type p53 tumor suppressor cDNA for replacement of the missing or damaged p53 gene associated with over 50% of human cancers, including those of the lung, breast, prostate and colon.

Since the therapeutic specificity of the resulting recombinant AAV vector is determined by the plasmid introduced, the same packaging cell line can be used for any of these applications. The plasmid comprising the specific target polynucleotide is introduced into the packaging cell for production of the AAV vector by one of several possible methods; including, for example, electroporation.

Helper virus can be introduced before, during or after introduction of the rAAV vector. For instance, the plasmid can be co-infected into the culture along with the helper virus. The cells are then cultured for a suitable period, typically 2–5 days, in conditions suitable for replication and packaging as known in the art (see references above and examples below). Lysates are prepared, and the recombinant AAV vector particles are purified by techniques known in the art.

In a preferred embodiment, also illustrated in the Examples below, the recombinant AAV vector is itself stably integrated into a packaging cell line. Such stable, vector-containing packaging lines can also optionally contain stable chromosomal or episomal packaging cassettes. Cell lines such as those described above can be grown and stored until ready for use. To induce production of rAAV particles, the user simply infects the cells with helper virus and cultures the cells under conditions suitable for replication and packaging of AAV (as described below).

Recombinant AAV vectors prepared using the methods and compositions of the present invention can be purified according to techniques known in the art, see, e.g., the various AAV references cited above. Alternatively, improved purification techniques can be employed, such as those described by Atkinson et al. in a commonly-owned U.S. application entitled Methods for Generating High Titer Helper-Free Preparations of Recombinant AAV Vectors, filed Sep. 5, 1997 (as U.S. Ser. No. 08/925,815, converted to U.S. Ser. No. 60/084,193).

The rAAV vectors can be used to deliver polynucleotides to target cells either in vitro or in vivo, as described in the references cited herein and in the art. For delivery in vivo, the rAAV vectors will typically be contained in a physiological suitable buffered solution that can optionally comprise one or more components that promote sterility, stability and/or activity. Any means convenient for introducing the vector preparation to a desired location within the body can be employed, including, for example, by intravenous or localized injection, by infusion from a catheter or by aerosol delivery.

EXAMPLES

. A Generation of an Integrated AAV Packaging Cassette for rAAV Production

A 1. Construction of an AAV Packaging Cassette Employing P1 as an Exemplary Activating Element We have found that a P1 sequence, as found within a region believed to be an AAV integration locus on human chromosome 19, can be used as an activating element within the context of the present invention. The exemplary P1 sequence we used comprises nucleotides 354–468 of the AAV S1 locus (Kelman et al (1994) Curr. Opin. Genet. Dev. 4:185–195 also Weitzman et al (1994) Proc. Natl. Acad. Sci. 91:5808–5817). Shown below is the nucleotide sequence of P1 (SEQ ID NOs. 1 and 2), including a presumed terminal resolution site (TRS) at nucleotides 372–377, and a presumed Rep binding motif (RB Motif, also known as a Rep-binding site or RBS), at nucleotides 386–401. Also indicated (by the downward-pointing arrow) is the presumed Rep cleavage site located between the thymidines of the TRS.

A 2. Construction of p5repcap

As an exemplary AAV packaging cassette, we linked a P1 element (as described above) to AAV rep and cap genes that remained operably linked to their native AAV promoters. As a first step in that process, an AAV packaging cassette, p5repcap, comprising the AAV rep and cap encoding sequences transcriptionally linked to the native p5, p19 and p40 promoters and followed by the AAV2 polyadenylation signal, was constructed as follows. Briefly, a fragment from pAV2 comprising nucleotides 193 to 379 (Srivastiva et al. (1983) J. Virol. 45:555–564) was obtained by PCR amplification. The design of the PCR primers resulted in addition of a BglII site at the 5' end of the amplified fragment and encompassed the PpuMI site (at AAV-2 nucleotide 350) close to the 3' end. The PCR-amplified DNA was digested with BglII and PpuMI to generate a restriction fragment comprising AAV-2 nucleotides 193–350. A restriction fragment comprising nucleotides 351–4498 of pAV2 was isolated from pAV2 by digestion with PpuMI and SnaBI. These two fragments (representing nucleotides 193–4498 of pAV2) were ligated into a tgLS(+)HyTK retroviral vector (S. D. Lupton et al., Molecular and Cellular Biology, 11: 3374–3378, 1991) in a four-way ligation that also included a StuI-BstEII fragment of tgLS(+)HyTK and a BstEI-StuI fragment of tgLS(+)HyTK to which a BglII linker had been attached at the StuI end. This ligation generated tgLS(+) HyTK-repcap. Subsequently, a BglII-ClaI fragment from tgLS(+)HyTK-repcap, including AAV rep and cap genes transcriptionally linked to the native p5, p19 and p40 promoters and followed by the AAV2 polyadenylation signal, was isolated and cloned into the BamHI and ClaI sites of pSP72 (Promega).

A 3. Construction of p5repcapDHFR

An AAV packaging expression plasmid, p5repcapDHFR, was constructed for the purpose of producing an integrated packaging line including the construct p5repcap (Example A 2) and a modified dihydrofolate reductase gene (DHFR) as a selectable marker. Specifically, p5repcap (Example A 2) was linearized at a PvuII site located just upstream of the rep gene, and blunt-end ligated to a 1.8 kb fragment of pFR400 (Simonsen et al. (1983) Proc. Natl. Acad. Sci. USA 80:2495–2499). This pFR400 fragment was comprised of a modified DHFR gene, with a reduced affinity for methotrexate (Mtx), transcriptionally linked to the SV40 early promoter and followed by the polyadenylation site from the Hepatitis B virus (HBV) surface antigen gene. The pFR400 fragment was prepared by first digesting with SalI, followed by a four base pair fill-in (to generate a blunt end) and subsequent PvuII digestion and gel purification. The resulting construct, p5repcapDHFR (FIG. 1), contains a DHFR gene whose transcription is regulated by an upstream SV40 early promoter and a downstream Hepatitis B Virus polyadenylation site. Immediately downstream of this DHFR transcriptional cassette lie the AAV rep and cap genes, followed by an AAV polyadenylation site.

A 4. Addition of P1 to a repcap-Containing Plasmid: Construction of P1RCD

Figure 2:
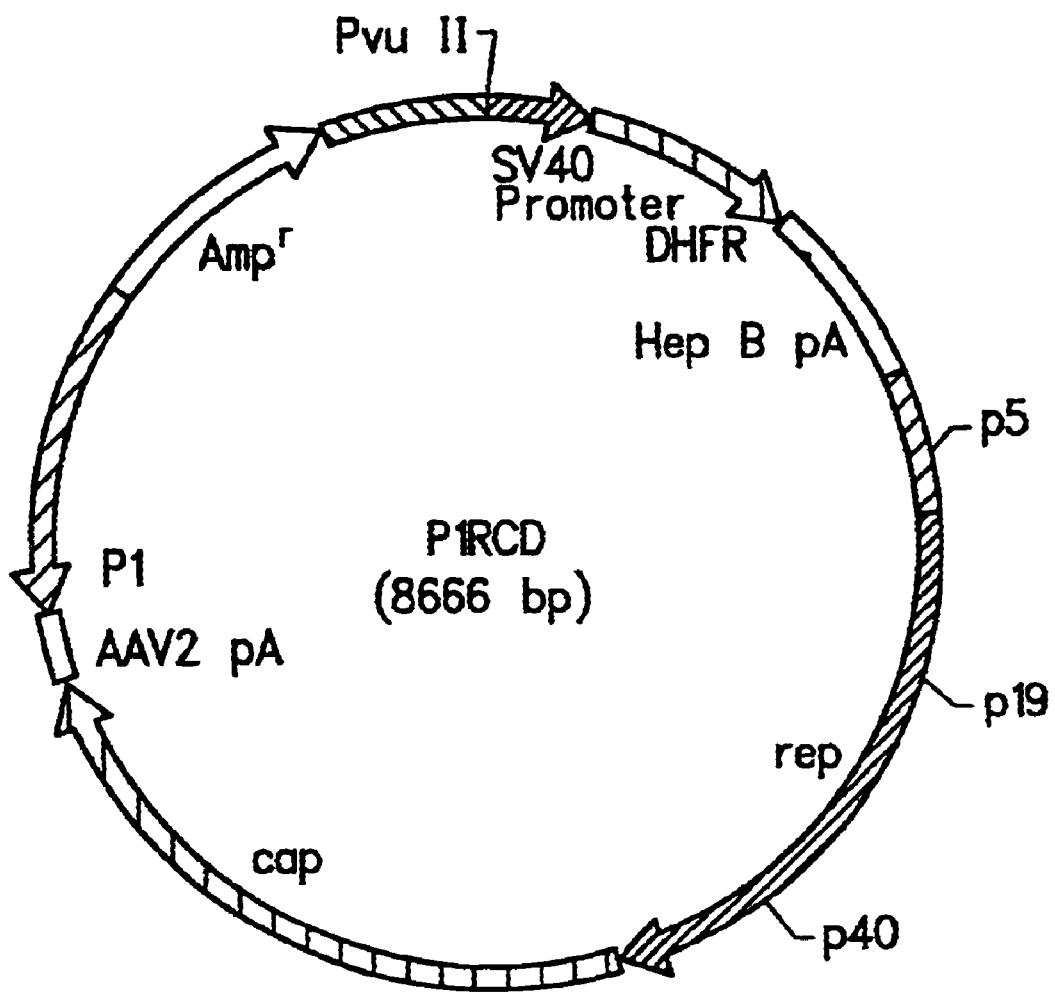
FIG. 2 shows a map of the P1RCD plasmid.

An exemplary AAV packaging cassette was then generated by incorporating a P1 element (Example A 1) into expression plasmid p5repcapDHFR (Example A 3). In the construction of the plasmid, "P1RCD", containing this packaging cassette, the P1 element was inserted downstream of the AAV polyadenylation signal in p5repcapDHFR in an orientation such that replication initiating from the P1 element proceeds first into the cap gene and then into the rep gene (i.e., replication initiates at the 3'-OH of the TRS on the anti-sense strand and proceeds in a 5'-to-3' direction towards the cap gene). To facilitate insertion of the P1 element into p5repcapDHFR, a pair of oligonucleotides were synthesized which include the P1 sequence flanked by ends compatible with a BglII restriction site (see sequences below, SEQ ID NOs. 3 and 4). The pair were annealed, then ligated to p5repcapDHFR previously linearized at a BglII site located just downstream of the AAV polyadenylation site (Example A 3, nucleotide 6217). A clone named P1RCD was selected, containing a P1 insert in an orientation such that replication initiated at P1 proceeds in the direction of the cap and rep genes (FIG. 2).

Additional exemplary constructs were produced in which the location and multiplicity of the P1 element was varied. P1(5')RCD contained a single P1 element upstream of the rep and cap genes at a distance of 1.5 kilobases from the rep translation initiation site. The construct 2P1RCD contained two P1 elements: the first located immediately downstream of cap as in P1RCD (see above) and the second inserted 1.5 kb upstream of rep as in P1(5')RCD described above.

Insertion of a P1 element into p5repcapDHFR to generate P1(5')RCD, and into P1RCD to generate 2P1RCD, was performed in a manner analogous to that described above for insertion of a P1 element into p5repcapDHFR to generate P1RCD, except that the oligonucleotide pair listed below (SEQ ID NO 5) was used. The new oligo pair was annealed and ligated into p5repcapDHFR and P1RCD previously linearized at the Pvu II site located 1.5 kilobases upstream of the rep translation initiation codon. Clones were selected such that the orientation of the P1 insert resulted in DNA replication proceeding first into the rep gene and then into cap.

P1 oligo pair for construction of P1(5')RCD and 2P1RCD

SEQ ID NO 5:
```
                                   TRS
5' CCCGGGCGGGTGGTGGCGGCGGTTGGGGCTCGGCGCTCGCTCGCTCGCTGGGCGGGCGGGCGGTCAG 3'
   ||||||||||||||||||||||||||||||||||||||||||||||||||||||||||||||||||
3' GGGCCCGCCCACCACCGCCGCCAACCCCGAGCCGCGAGCGAGCGAGCGACCCGCCCGCCCGCCAGTC 5'
                                    RB Motif
```

Additional exemplary packaging plasmids were constructed that contained P1 elements in constructs lacking a selectable marker. Construct P1(5')RC contained a single P1 element immediately upstream of the rep and cap genes; P1RC contained a single P1 element immediately downstream from the rep and cap genes; and 2P1RC contained two P1 elements flanking rep-cap. The constructs were produced as described above in this example except that AAV packaging construct p5repcap (Example A2) was used in place of AAV packaging construct p5repcapDHFR. The P1 sequence was inserted as described above in this example using both of the oligo pairs described above, as appropriate. Virus was produced by co-transfection of either p5repcap, P1RC, P1(5')RC, or 2P1RC along with rAAV vector ACAPSN according to the method of Example A6, infra. Virus titer was measured for each using the method of Example A7, infra.

A 5. Construction of rAAV Vector ACAPSN

The plasmid ACAPSN was constructed according to Lynch et al. (1997) Circ. Res. 80: 497–505 and PCT Publication WO 97/32990, as follows. The ITR sequences and plasmid backbone were derived from AAV-CFTR. Afione et al. (1996) J. Virol. 70:3235–3241. Briefly, the AAV-CFTR vector was digested with XhoI and SnaBI and the ITRs and plasmid backbone were gel isolated. An XhoI to SnaBI fragment containing a portion of the CMV promoter (nucleotides −671 to −464) [See, e.g., Boshart, et al., Cell, 41: 521–530 (1985)] was gel isolated and ligated to the ITR plasmid backbone fragment derived from AAV-CFTR to generate "pAAV-CMV (SnaBI)." Next, an SpeI to SnaBI fragment containing the synthetic polyadenylation signal was inserted into SpeI/SnaBI digested pAAV-CMV (SnaB1) to generate "pAAV-CMV (SpeI)-spA." The pAAV-CMV (SpeI)-spA vector contains nucleotides −671 to −584 of the CMV promoter. Next, the human placental alkaline phosphatase cDNA sequence linked to the Simian virus 40 promoter driving the E. coli neomycin gene was isolated from LAPSN [See, e.g., Clowes et al. (1994) J. Clin. Invest. 93: 644–651] as an SpeI to NheI fragment and inserted into pAAV-CMV (SpeI)-spA (which had been linearized with SpeI) to create "pAAV-APSN." An SpeI to NheI fragment containing CMV promoter nucleotides −585 to +71 was inserted into SpeI-linearized pAAV-APSN to generate vector "ACAPSN."

A 6. Virus Production

Packaging of rAAV particles was performed as previously described. See, e.g., Flotte et al., *J. Biol. Chem.* 268 (5): 3781–3790 (1993); Flotte et al., *Proc. Natl. Acad. Sci. USA*, 93: 10163–10167 (1993); and Flotte et al. (1995) Gene Ther. 2:29–37. According to these protocols, equal amounts of packaging plasmids (either p5repcapDHFR or P1RCD) and the rAAV vector ACAPSN were co-transfected into HeLa cells which had been infected with helper Ad 5 at a MOI of 5. After incubation for 65 hours at 37° C. in a humidified atmosphere of 10% $CO_2$, cells were harvested and lysed by freeze/thawing and sonication. Cell debris was removed by centrifugation at 3000×g for 5 minutes. The resulting cleared lysates were heat-treated for 1 hour at 56° C. to inactivate residual adenovirus.

A 7. Measurement of Virus Titer by G418 Resistance

Methods The titer of virus produced by the method in Example A 6 from co-transfection of ACAPSN and either the pSrepcapDHFR or P1RCD AAV packaging plasmid was determined by the measurement of geneticin (G418) resistance. The protocol includes seeding $5 \times 10^4$ HeLa cells per well in a 6 well dish (Costar) in Dulbecco's Modified Eagles medium, 10% fetal bovine serum, with penicillin and streptomycin (DMEM complete). After 24 hours, cells were exposed to serial dilutions (in DMEM) of virus-containing cleared lysates (Example A 6) for 24 hours at 37° C. in a total volume of 1 ml (the maximal amount of cleared lysate that is assayable being 0.1 ml). Virus-containing medium was then removed and fresh DMEM, containing 1 mg/ml G418, was added to the cells. Cells were cultured for 10 days under selective conditions, medium was then removed, and the cells were washed once in methanol and stained with methylene blue. Colonies on each well were then counted and results expressed as G418-resistant colony forming units per milliliter ($G418^r$ cfu/ml).

Results The packaging plasmids P1(5')RCD, P1RCD and 2P1RCD (see Example A 4) were assayed for their ability to produce virus in a co-transfection with rAAV vector ACAPSN. Co-transfection, helper virus infection and preparation of cleared lysates were performed as described in Example A6.

The construct containing a single P1 element downstream of cap (P1RCD) produced four-fold more virus than the non-P1 containing construct, p5repcapDHFR (1900+/−1400 cfu/mL vs. 490+/−58 cfu/mL, respectively). When the P1 element was located at a distance of 1.5 kb upstream of the rep-cap gene cassette (P1(5')RCD), a 20-fold increase in virus production was observed relative to the non-P1 construct, p5repcapDHFR (9900+/−1000 cfu/mL vs 480+/−58 cfu/mL, respectively). Incorporating both P1 elements, such that one was located 1.5 kb upstream of rep and the other was immediately downstream of cap, resulted in a further increase in virus production (17,500+/−2000 cfu/mL), i.e. 36-fold compared to p5repcapDHFR.

The AAV packaging constructs lacking a DHFR marker containing a single P1 element either immediately upstream or downstream of the rep and cap genes (P1 (5')RC or P1RC, respectively, see Example A 4) resulted in a 3 fold increase in rAAV vector titer compared to the non-P1 containing construct, p5repcap (5500+/−1514 Cfu/ml or 5700+/−1172 vs. 1700+/−560 Cfu/ml). Incorporating both P1 elements flanking the rep and cap genes (2P1RC, see Example A 4) further increased virus production 10-fold compared to the single P1-containing constructs (53000+/−8082 Cfu/ml), equivalent to a 30-fold increase in viral titer compared to the non-P1 containing construct, p5repcap. These results show that P1 functions to amplify vector production, independent of location or distance from the rep-cap gene cassette, when tested in transient co-transfection.

A 8. Production of Packaging Cell Lines

Polyclonal cell lines with an integrated AAV packaging cassette either containing (P1RCD) or lacking (p5repcapDHFR) the P1 element were produced by electroporation of HeLa cells. Specifically, $4 \times 10^6$ HeLa cells were electroporated with 12 µg DNA (p5repcapDHFR or P1RCD) that had been linearized with PvuII restriction endonuclease, which cleaves just upstream of the SV40 promoter-DHFR gene cassette. The cells were electroporated in serum free DMEM using a BioRad Gene Pulser at 0.25 Volts and 960 µF. After electroporation, cells were resuspended in DMEM complete (see Example A 7) and allowed to recover at 37° C. in a humidified atmosphere of 10% $CO_2$. After 24 hours, cells were subjected to selection in complete medium containing 500 nM methotrexate. Clonal cell lines were derived from the P1RCD polyclonal population by limiting dilution. Producer lines are generated by introduction of an rAAV vector construct into a clonal P1RCD-containing packaging line.

The constructs p5repcap, P1RC, P1(5')RC, and 2P1RC (see Example A 4) were modified for the purpose of producing stable cell lines by following the procedure described in Example A 3, using a puromycin resistance gene in place of the modified DHFR gene. The four resulting AAV packaging constructs were named p5RC-Pur, P1RC-Pur, P1(5')RC-Pur, and 2P1RC-Pur. Polyclonal cell lines were produced from these four constructs as described above in this example, except the methotrexate selection was replaced with drug selection by puromycin at a concentration of 1 µg/mL.

A 9. Isolation of Total Genomic DNA From Packaging Cells rAAV genomes were packaged according to Example A 6 in polyclonal cell lines containing either p5repcapDHFR or P1RCD (Example A 8) by transfection with ACAPSN in the presence or absence of adenovirus. At 65 hours after transfection with ACAPSN, cells were harvested and centrifuged at 3000×g for 5 minutes. Total genomic DNA was isolated according to the method previously reported (Sambrook et al., supra). Specifically, cells were washed once with TBS (150 mM Trizma base, 300 mM NaCl, pH 7.4) and resuspended in TNE Buffer (10 mM Tris-Cl pH 8, 100 mM NaCl and 25 mM EDTA pH 8). Proteinase K was added to a final concentration of 100 µg/ml and SDS was added to a final percentage of 0.5% (w/v). After mixing, cells were incubated at 50° C. for 3 hours. Samples were then extracted once with phenol (pH 8), once with phenol:chloroform:isoamyl alcohol (24:24:1), and once with chloroform. DNA, present in the aqueous phase, was then precipitated with 100% ethanol and centrifuged at 12,000×g for 30 minutes. The pellets, containing genomic DNA, were washed once with 70% ethanol, air dried, and resuspended in TE buffer (10 mM Tris, 1 mM EDTA pH 8).

10. Southern Blotting Analysis

Total genomic DNA isolated by the method of Example A 9 was examined for the amplification of rep and cap genes in the presence and absence of adenovirus. Specifically, 10 µg of DNA was digested with restriction endonuclease BglI thereby releasing a 3.8 kb fragment comprising rep and cap genes (AAV-2 nucleotides 543–4,380) from p5repcapDHFR or P1RCD. Digested DNA samples were then fractionated by agarose gel electrophoresis and transferred to UV-Duralon membrane (Stratagene) by capillary action, overnight, in 10×SSC (1.5 M NaCl, 0.15M Sodium Citrate). Nucleic acid was cross-linked to the membrane by exposure to ultraviolet light, and the membranes were rinsed in 2×SSC and probed with a $^{32}$P labeled 1.9 kb XhoI-BglII fragment from pAV2, random-prime labeled using prime-it, Stratagene. After washing, the membranes were visualized by phosphorimaging and the amount of the 3.8 kb band was quantified.

A 11. Analysis of Packaging Cassette Amplification in Polyclonal Packaging Cell Lines Total genomic DNA prepared and digested according to Example A 9 for polyclonal samples P1RCD and p5repcapDHFR (Example A 8) was analyzed by the Southern blotting method of Example A 10. Degree of amplification was measured by relative photon intensity of the 3.8 kb band determined from phosphorimaging according to Example A 10. DNA from P1RCD-containing cells gave a value of 406,725 intensity units for the 3.8 kb band, while DNA from cells containing p5repcapDHFR gave a value of 30,211. Thus the presence of P1, in the P1RCD polyclonal line, is responsible for a 13.5-fold amplification of rep and cap genes, in the presence of adenovirus.

A 12. Virus Production by Packaging Cell Lines

Polyclonal cell lines, containing either P1RCD or p5repcapDHFR, were transiently transfected with ACAPSN in the presence of adenovirus, rAAV genomes were packaged, and cleared lysates were produced according to the method of Example A 6. Cleared lysates were assayed for viral titer (Example A 7), which was determined from triplicate transfections. When maximal amounts of cleared lysate were assayed (i.e., the amount at which non-specific cell killing begins to occur), a polyclonal cell line containing p5repcapDHFR yielded 0 G418$^r$ cfu/ml, while a polyclonal cell line containing P1RCD yielded 957 G418$^r$ cfu/ml. Virus production by clonal lines ranged from $0.8 \times 10^2$–$1.5 \times 10^4$ G418$^r$ cfu/ml.

Stable cell lines containing integrated P1-containing packaging plasmids expressing puromycin resistance were tested for virus production. A stable cell line containing a single P1 element downstream from the cap gene (P1RC-Pur) increased virus titer 4 fold over the non-P1 containing cell line, p5RC-Pur (216+/−67 Cfu/ml vs. 51.1+/−30 Cfu/ml). When the P1 element was located upstream of the rep gene (P1(5')RC-Pur), a similar increase in virus titer occurred (333 Cfu/ml +/−150), 6 fold over the non-P1 containing cell line, p5RC-Pur . The stable cell line containing 2 P1 elements flanking rep-cap (2P1RC-Pur), resulted in a further increase in viral titer (658+/−122 Cfu/ml) to 13-fold that of the non-P1 containing cell line, p5RC-Pur. These results show that P1 functions to amplify vector production in a stable cell line, regardless of its location.

B. Use of an Episomally-maintained AAV Packaging Cassette for rAAV Production

B 1. Construction of an EBNA-1 Based AAV Packaging Vector Containing P1 Elements The EBNA-1 episomal packaging cassette containing AAV rep and cap genes along with two P1 elements was constructed in the following manner. Two 69 bp oligonucleotides containing the published P1 sequence (Urcelay et al. (1995) *J. Virol.* 69:203846) were synthesized. In addition to the P1 sequence, the oligonucleotides contain a unique SmaI restriction site. After annealing, the SphI-compatible oligonucleotides were inserted into the SphI site of the p5repcap vector (Example A 2). A clone containing two opposing concatameric P1 elements (TRS-RBS-RBS-TRS) was obtained.

Figure 3:
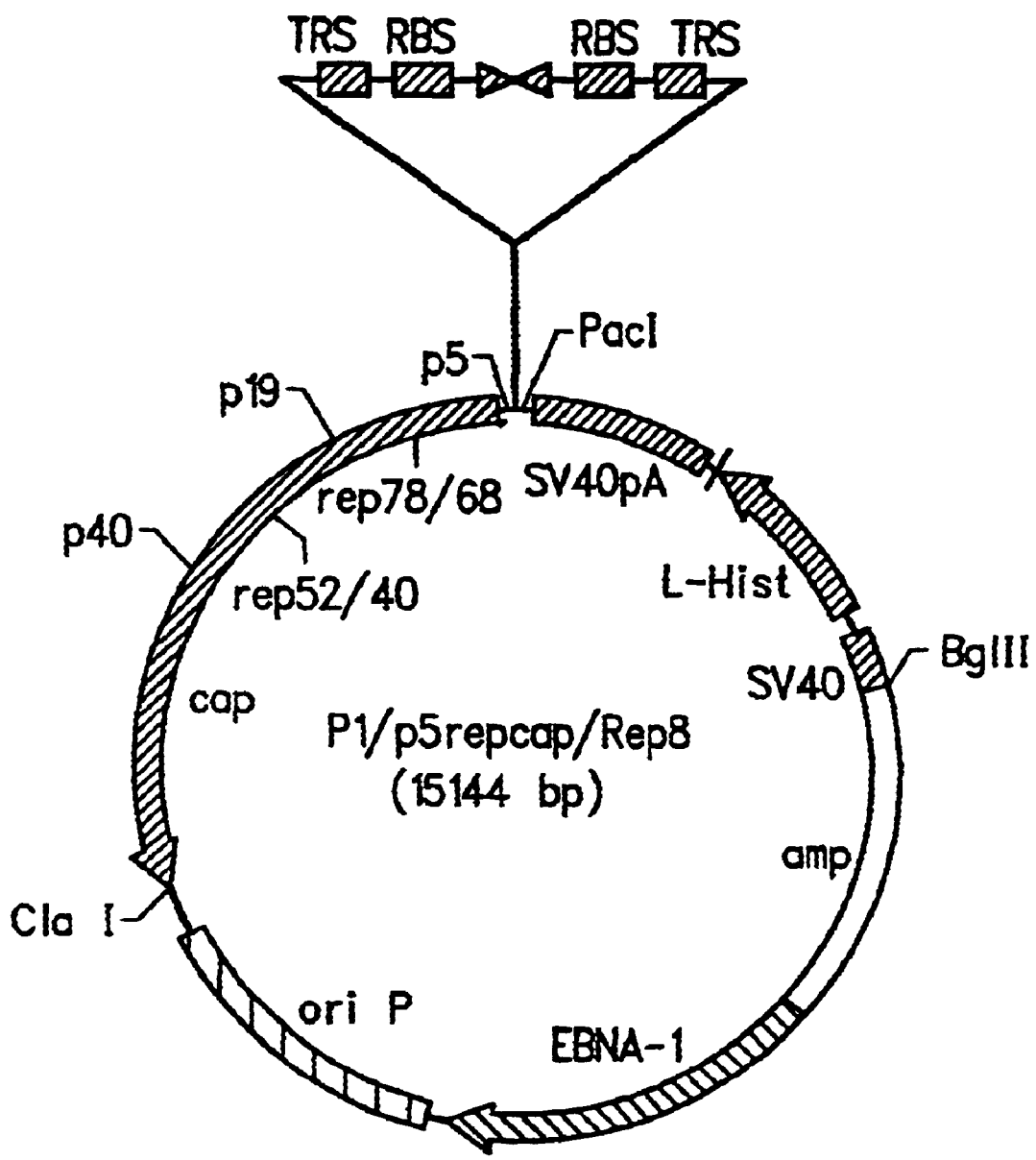
FIG. 3 shows a map of the episomal packaging plasmid P1/p5repcap/Rep8. The concatameric P1 elements (at "12 o'clock" on the circle) are indicated. Each P1 element comprises a terminal resolution site (TRS) and a Rep-binding site (RBS, also known as a Rep-binding motif or RB Motif). The p5repcap(–P1)/Rep8 construct is identical except that it does not contain the concatameric P1 elements.

A 4424 bp PvuII/BglII fragment containing the two P1 elements and p5repcap sequences was isolated. These sequences were inserted into the NruI/BamHI-digested Rep8 EBNA-1 plasmid (Invitrogen). The resulting plasmid was designated P1/p5repcap/Rep8. In this construct, the tandem P1 sequences are located 84 nucleotides upstream of the p5 promoter and the associated rep and cap genes (FIG. 3).

In addition, a p5repcap/Rep8 plasmid that did not contain a P1 element was constructed by isolating a 4355 bp PvuII/BglII fragment from the p5repcap vector. This fragment was inserted into NruI/BamHI digested Rep8. The resulting plasmid was designated pSrepcap(−P1)/Rep8.

B2. Generation of Cell Lines Containing a Stably-integrated rAAV Vector and an Episomal P1 AAV Packaging Cassette The rAAVCFTR or ACAPSN vector was transfected into HeLa cells via electroporation. Individual clones were isolated and screened for an intact, stably integrated rAAV vector. The P1/pSrepcap/Rep8 packaging cassette was then transfected into HeLa/AAV-CFTR cells via $CaHPO_4$-mediated transfection and stable transfectants were selected using 2.5 mM L-histidinol. A HeLa/AAV-CFTR cell line containing a p5repcap(−P1)/Rep8 packaging cassette was generated in similar fashion.

B 3. Amplification of P1-containing Episomal Packaging Cassette

Figure 4:
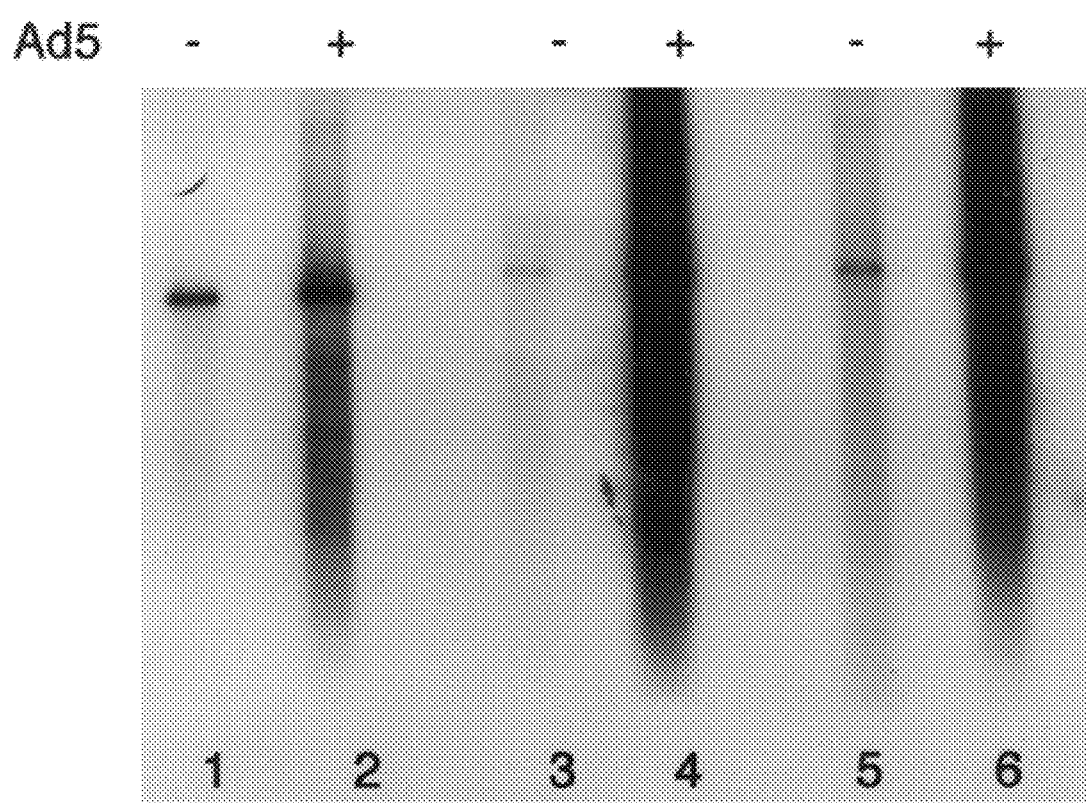
FIG. 4 shows phosphorimaging analysis of a Southern blot to assay levels of the episomal P1-containing packaging plasmid in the presence (+) or absence (–) of Ad5 infection. Lanes 1 and 2—HeLa cells containing the episomal packaging plasmid p5repcap(–P1)/Rep8. Lanes 3 and 4, 5 and 6—HeLa cells containing the episomal packaging plasmid P1/p5repcap/Rep8.

To determine if the P1/p5repcap/Rep8 packaging cassette is amplifiable in stable HeLa/AAV-CFTR cell line, the following experiment was carried out. The stable HeLa/AAV-CFTR cell line from Example B 2 were seeded in duplicate at $2.5 \times 10^5$ cells/plate. After 24 hrs one plate for each cell line was infected with Ad5 at a multiplicity of 10. After 48 hrs. infected and uninfected cells were harvested. The genomic DNA was isolated, digested with BglII and XbaI restriction enzymes, and the resultant fragments were separated by electrophoresis and transferred to a membrane. The blot was then probed with a $^{32}$P-labeled 2.0 kb rep fragment and the degree of amplification was determined by Southern blotting as described in Example A 10. The results are shown in FIG. 4 and indicate that in the presence of adenovirus the P1-episomal packaging cassette exhibits a high degree of amplification (10 to 100 fold increase), whereas in the absence of adeno virus no amplification is observed. The p5repcap(−P1) episomal packaging cassette exhibited very little detectable amplification in the presence and no detectable amplification in the absence of adenovirus.

Figure 5:
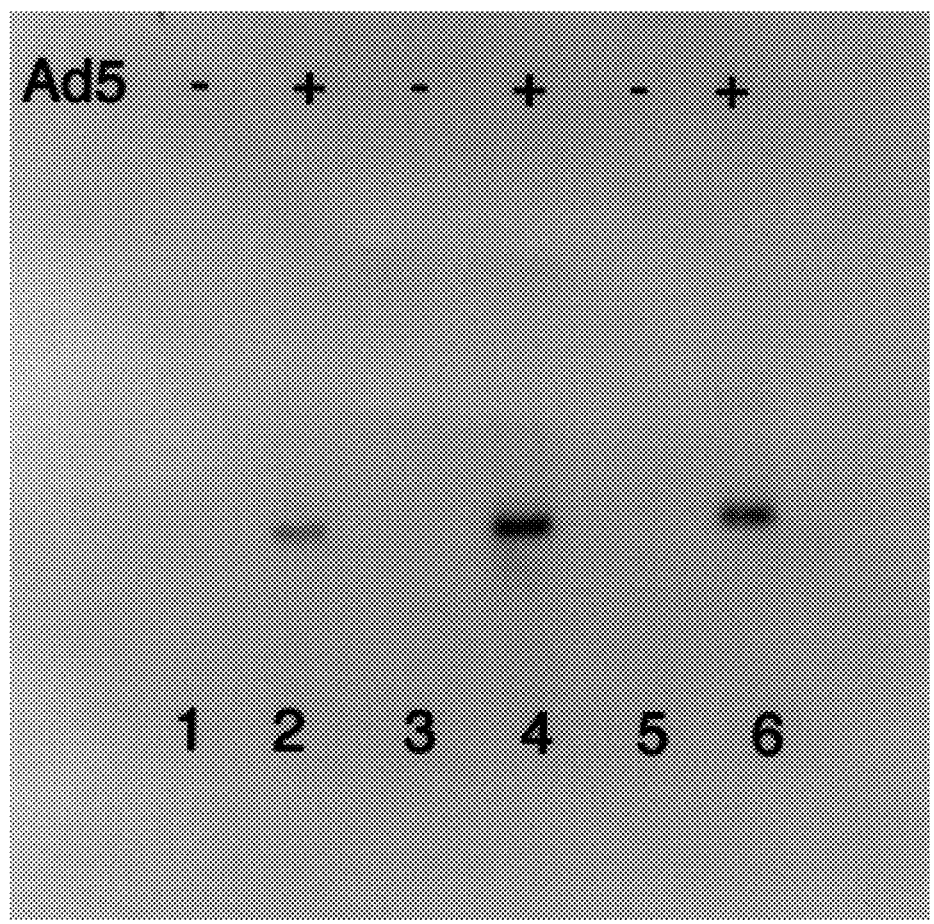
FIG. 5 shows phosphorimaging analysis of a Southern blot to assay rAAV-CFTR production in cells containing the episomal packaging plasmids p5repcap(–P1)/Rep8 and P1/p5repcap/Rep8, in the presence (+) or absence (–) of Ad5 infection. Lanes 1 and 2—HeLa cells containing the episomal packaging plasmid p5repcap(–P1)/Rep8. Lanes 3 and 4, 5 and 6—HeLa cells containing the episomal packaging plasmid P1/p5repcap/Rep8.

B 4. Production of rAAV-CFTR Vector in HeLa/AAV-CFTR Cell Line Containing a P1/p5repcap/Rep8 Packaging Cassette To demonstrate rAAV virus production in a HeLa/AAV-CFTR cell line containing a P1/p5repcap/Rep8 episomal packaging cassette, the following experiment was carried out. See PCT Publication WO 96/17947 for details. Briefly, HeLa/AAV-CFTR cells containing either a P1/p5repcap/Rep8 or a p5repcap(−P1)/Rep8 episomal packaging cassette were seeded at $2.5 \times 10^6$ cells/plate and infected with Ad5 at a MOI of 10. After 48 hrs., the cells were harvested, resuspended in TMEG buffer, and sonicated in 15-second bursts for 2 min. to release rAAV. One percent of the crude lysate was heat-treated at 56° C. for 45 min and then added to $2.5 \times 10^5$ cl.37 cells, with or without Ad5. The cells were harvested after 48 hrs and genomic DNA was isolated. The DNA was digested with EcoRI, resolved by electrophoresis, transferred to a membrane and probed with a $^{32}$p-labeled 1.4 kb CFTR fragment. Results are shown in FIG. 5 and indicate that in the presence of Ad5 the cell line containing the P1/p5repcap/Rep8 packaging cassette was producing at least 10 times more virus than the cell line containing the p5repcap(−P1)/Rep8 packaging cassette.

B 5. P1-EBNA Vector Variations

To reduce the potential for generating wild type AAV or replication-competent chimeric AAV, a second generation P1/p5repcap/Rep8 packaging cassette was constructed that contains a nonessential 1300 bp DNA stuffer fragment between the P1 elements and the p5repcap sequences. To construct this packaging cassette, a 4355 bp PvuII/EcoRV fragment containing p5repcap sequences was isolated from the p5repcap vector (Example A 2). This fragment was inserted at the EcoRV site of pAdBn (Quantum Biotechnologies). The resulting plasmid was digested with BglII and NotI and a 4485 bp p5repcap fragment was isolated. This BglII/NotI fragment was inserted into BamHI/NotI-digested pRep8 (Invitrogen).

To insert the two concatameric P1 elements into this plasmid the P1/p5repcap/Rep8 packaging cassette (see Example B 1) was digested with PstI to remove the p5repcap sequences. The plasmid backbone, containing the two P1 elements, was religated. The resulting plasmid was digested with PvuII and NotI, and a 138 bp fragment, containing concatameric P1 sites, was isolated. This P1 dimer was then inserted into P1/p5repcap/Rep$^8$ that had been digested with NruI and NotI. Finally, to insert the nonessential stuffer fragment, a 1300 bp HaeIII fragment from Φ174 was ligated into the SnaI site of P1/p5repcap/Rep$^8$. The resulting plasmid is used as an AAV packaging cassette to stimulate replication and packaging of rAAV vectors.

While the invention has been described, for purposes of clarity and illustration, with reference to the description and examples above, it is clear that many variations and modifications can be made by one of skill in the art, without departing from the scope of the appended claims.

What is claimed is:

1. A recombinant polynucleotide comprising a sequence encoding an adeno-associated virus (AAV) packaging cassette comprising at least one AAV rep and/or cap gene amplifiably linked to a P1 element.

2. The recombinant polynucleotide of claim 1, wherein the AAV packaging cassette comprises an AAV rep gene and an AAV cap gene amplifiably linked to a P1 element.

3. The recombinant polynucleotide of claim 1, wherein the P1 element comprises the sequence of SEQ ID NO:1.

4. The recombinant polynucleotide of claim 1, wherein the AAV packaging cassette comprises an AAV rep gene amplifiably linked to a P1 element.

5. The recombinant polynucleotide of claim 2, wherein the P1 element comprises the sequence of SEQ ID NO:1.

6. A method for producing high-titer stocks of an rAAV vector containing a heterologous gene of interest, comprising co-expressing the rAAV vector containing the heterologous gene of interest in a mammalian cell along with an AAV packaging cassette, said AAV packaging cassette comprising at least one AAV rep and/or cap gene amplifiably linked to a P1 element; and incubating the cell under conditions that allow production of high-titer stocks of the rAAV vector.

7. The method of claim 6, wherein the P1 element comprises the sequence of SEQ ID NO:1.

8. The method of claim 6, wherein the AAV packaging cassette comprises an AAV rep gene amplifiably linked to a P1 element.

9. The method of claim 6, wherein the AAV packaging cassette comprises an AAV rep gene and an AAV cap gene amplifiably linked to a P1 element.

10. A method for generating a cell line capable of producing high-titer stocks of an rAAV vector containing a heterologous gene of interest, comprising transfecting mammalian cells with an rAAV vector containing the heterologous gene of interest and with an AAV packaging cassette, said AAV packaging cassette comprising at least one AAV rep and/or cap gene amplifiably linked to a P1 element, whereby the cell line capable of producing high-titer stocks of the rAAV vector is generated.

11. The method of claim 10, wherein the P1 element comprises the sequence of SEQ ID NO:1.

12. The method of claim 10, wherein the AAV packaging cassette comprises an AAV rep gene amplifiably linked to a P1 element.

13. The method of claim 10, wherein the AAV packaging cassette comprises an AAV rep gene and an AAV cap gene amplifiably linked to a P1 element.

14. An AAV packaging cell line comprising mammalian cells transfected with a rAAV vector containing a heterologous gene of interest and with an AAV packaging cassette, said AAV packaging cassette comprising at least one AAV rep and/or cap gene amplifiably linked to a P1 element.

15. The AAV packaging cell line of claim 14, wherein the P1 element comprises the sequence of SEQ ID NO:1.

16. The AAV packaging cell line of claim 14, wherein the AAV packaging cassette comprises an AAV rep gene amplifiably linked to a P1 element.

17. The AAV packaging cell line of claim 14, wherein the AAV packaging cassette comprises an AAV rep gene and an AAV cap gene amplifiably linked to a P1 element.

18. An AAV packaging cell comprising an AAV packaging cassette comprising at least one AAV rep and/or cap gene amplifiably linked to a P1 element.

19. The AAV packaging cell of claim 18, wherein the AAV packaging cassette is integrated into a chromosome of the cell.

20. The AAV packaging cell of claim 18, wherein the AAV packaging cassette propagates episomally.

21. The AAV packaging cell of claim 18, wherein the P1 element comprises the sequence of SEQ ID NO:1.

22. The AAV packaging cell of claim 18, wherein the AAV packaging cassette comprises an AAV rep gene amplifiably linked to a P1 element.

23. The AAV packaging cell of claim 18, wherein the AAV packaging cassette comprises an AAV rep gene and an AAV cap gene amplifiably linked to a P1 element.

24. A method of making a packaging cell according to claim 18, said method comprising transfecting a host cell with a recombinant polynucleotide according to claim 1.

* * * * *

UNITED STATES PATENT AND TRADEMARK OFFICE
CERTIFICATE OF CORRECTION

PATENT NO. : 6,642,051 B1 Page 1 of 1
DATED : November 4, 2003
INVENTOR(S) : Carmel M. Lynch et al.

It is certified that error appears in the above-identified patent and that said Letters Patent is hereby corrected as shown below:

Column 32,
Line 42, please replace "Φ174" with -- ΦX174 --.

Signed and Sealed this

Third Day of February, 2004

JON W. DUDAS
*Acting Director of the United States Patent and Trademark Office*

SEQUENCE LISTING

<160> NUMBER OF SEQ ID NOS: 5

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: AAV
      vectors

<400> SEQUENCE: 1

```
cgggcgggtg gtggcggcgg ttggggctcg gcgctcgctc gctcgctggg cgggcgggcg    60
gt                                                                   62

<210> SEQ ID NO 2
<211> LENGTH: 62
<212> TYPE: DNA
<213> ORGANISM: Artificial Sequence
<220> FEATURE:
<223> OTHER INFORMATION: Description of Artificial Sequence:  AAV
      vectors

<400> SEQUENCE: 2
accgcccgcc cgcccagcga gcgagcgagc gccgagcccc aaccgccgcc accaccccgcc   60 cg                                                                   62

<210> SEQ ID NO 3
<211> LENGTH: 73
<212> TYPE: DNA
<213> ORGANISM: Artificial Sequence
<220> FEATURE:
<223> OTHER INFORMATION: Description of Artificial Sequence:  AAV
      vectors

<400> SEQUENCE: 3
gatcactagt accgcccgcc cgcccagcga gcgagcgagc gccgagcccc aaccgccgcc    60 accaccccgcc cga                                                      73

<210> SEQ ID NO 4
<211> LENGTH: 74
<212> TYPE: DNA
<213> ORGANISM: Artificial Sequence
<220> FEATURE:
<223> OTHER INFORMATION: Description of Artificial Sequence:  AAV
      vectors

<400> SEQUENCE: 4
agatctcggg cgggtggtgg cggcggttgg ggctcggcgc tcgctcgctc gctgggcggg    60
cgggcggtac tagt                                                      74

<210> SEQ ID NO 5
<211> LENGTH: 67
<212> TYPE: DNA
<213> ORGANISM: Artificial Sequence
<220> FEATURE:
<223> OTHER INFORMATION: Description of Artificial Sequence:  AAV
      vectors

<400> SEQUENCE: 5
cccgggcggg tggtggcggc ggttggggct cggcgctcgc tcgctcgctg ggcgggcggg    60
cggtcag                                                              67
```